(12) United States Patent
Boles et al.

(10) Patent No.: US 10,308,692 B2
(45) Date of Patent: Jun. 4, 2019

(54) VARIANTS OF GAL2 TRANSPORTER AND THEIR USES

(71) Applicant: Johann Wolfgang Goethe-Universität Frankfurt, Frankfurt am Main (DE)

(72) Inventors: Eckhard Boles, Darmstadt (DE); Alexander Farwick, La Madeleine (FR); Ferdinand Kirchner, Darmstadt (DE); Virginia Schadeweg, Frankfurt (DE); Mislav Oreb, Frankfurt (DE)

(73) Assignee: Lallemand Hungary Liquidity Management LLC, Budapest (HU)

( * ) Notice: Subject to any disclaimer, the term of this patent is extended or adjusted under 35 U.S.C. 154(b) by 0 days.

(21) Appl. No.: 15/520,814

(22) PCT Filed: Oct. 22, 2015

(86) PCT No.: PCT/EP2015/074519
§ 371 (c)(1),
(2) Date: Apr. 20, 2017

(87) PCT Pub. No.: WO2016/062821
PCT Pub. Date: Apr. 28, 2016

(65) Prior Publication Data
US 2017/0334955 A1  Nov. 23, 2017

(30) Foreign Application Priority Data
Oct. 22, 2014 (EP) .................................. 14189927

(51) Int. Cl.
| | | |
|---|---|---|
| *C07K 14/395* | (2006.01) | |
| *C12N 15/81* | (2006.01) | |
| *C12P 7/10* | (2006.01) | |
| *C12P 7/12* | (2006.01) | |
| *C12N 1/18* | (2006.01) | |
| *C12N 9/12* | (2006.01) | |
| *C12N 9/90* | (2006.01) | |
| *C12N 9/92* | (2006.01) | |
| *C12N 15/52* | (2006.01) | |
| *C12N 15/90* | (2006.01) | |
| *C12P 7/06* | (2006.01) | |

(52) U.S. Cl.
CPC .............. *C07K 14/395* (2013.01); *C12N 1/18* (2013.01); *C12N 9/1205* (2013.01); *C12N 9/90* (2013.01); *C12N 9/92* (2013.01); *C12N 15/52* (2013.01); *C12N 15/81* (2013.01); *C12N 15/905* (2013.01); *C12P 7/06* (2013.01); *C12P 7/10* (2013.01); *C12P 7/12* (2013.01); *C12Y 207/01016* (2013.01); *C12Y 207/01017* (2013.01); *C12Y 501/03004* (2013.01); *C12Y 503/01003* (2013.01); *C12Y 503/01005* (2013.01); *Y02E 50/16* (2013.01); *Y02E 50/17* (2013.01)

(58) Field of Classification Search
None
See application file for complete search history.

(56) References Cited

FOREIGN PATENT DOCUMENTS

WO    2012/049173 A1    4/2012

OTHER PUBLICATIONS

Farwick et al., "Engineering of yeast hexose transporters to transport D-xylose without inhibition by D-glucose," *Proceedings of the National Academy of Sciences* 111(14), 14 pages, 2014.
Weierstall et al., "Cloning and characterization of three genes (SUT1-3) encoding glucose transporters of the yeast *Pichia stipitis*," *Molecular Biology* 31(3):871-883, 1999.
Young et al., "A molecular transporter engineering approach to improving xylose catabolism in *Saccharomyces cerervisiae*," *Metabolic Engineering* 14:401-411, 2012.

*Primary Examiner* — Antonio Galisteo Gonzalez
(74) *Attorney, Agent, or Firm* — Seed IP Law Group LLP

(57) ABSTRACT

The present invention relates to polypeptides which are Gal2 variants comprising at least one amino acid substitution at a position corresponding to M435, and optionally further amino acid substitution(s). The present invention further relates to nucleic acid molecules encoding the polypeptides and to host cells containing said nucleic acid molecules. The present invention further relates to a method for the production of bioethanol and/or other bio-based compounds, comprising the expression of said nucleic acid molecules, preferably in said host cells. The present invention also relates to the use of the polypeptides, nucleic acids molecule or host cells for the production of bioethanol and/or other bio-based compounds, and/or for the recombinant fermentation of biomaterial containing pentose(s), preferably D-xylose and/or L-arabinose.

18 Claims, 8 Drawing Sheets
Specification includes a Sequence Listing.

SEQUENCE LISTING

<160> NUMBER OF SEQ ID NOS: 17

<210> SEQ ID NO 1
<211> LENGTH: 574
<212> TYPE: PRT
<213> ORGANISM: Saccharomyces cerevisiae

<400> SEQUENCE: 1

```
Met Ala Val Glu Glu Asn Asn Met Pro Val Val Ser Gln Gln Pro Gln
1               5                   10                  15

Ala Gly Glu Asp Val Ile Ser Ser Leu Ser Lys Asp Ser His Leu Ser
            20                  25                  30

Ala Gln Ser Gln Lys Tyr Ser Asn Asp Glu Leu Lys Ala Gly Glu Ser
        35                  40                  45

Gly Pro Glu Gly Ser Gln Ser Val Pro Ile Glu Ile Pro Lys Lys Pro
    50                  55                  60

Met Ser Glu Tyr Val Thr Val Ser Leu Leu Cys Leu Cys Val Ala Phe
65                  70                  75                  80

Gly Gly Phe Met Phe Gly Trp Asp Thr Gly Thr Ile Ser Gly Phe Val
                85                  90                  95

Val Gln Thr Asp Phe Leu Arg Arg Phe Gly Met Lys His Lys Asp Gly
            100                 105                 110

Thr His Tyr Leu Ser Asn Val Arg Thr Gly Leu Ile Val Ala Ile Phe
        115                 120                 125

Asn Ile Gly Cys Ala Phe Gly Gly Ile Ile Leu Ser Lys Gly Gly Asp
    130                 135                 140

Met Tyr Gly Arg Lys Lys Gly Leu Ser Ile Val Val Ser Val Tyr Ile
145                 150                 155                 160

Val Gly Ile Ile Ile Gln Ile Ala Ser Ile Asn Lys Trp Tyr Gln Tyr
                165                 170                 175

Phe Ile Gly Arg Ile Ile Ser Gly Leu Gly Val Gly Gly Ile Ala Val
            180                 185                 190

Leu Cys Pro Met Leu Ile Ser Glu Ile Ala Pro Lys His Leu Arg Gly
        195                 200                 205

Thr Leu Val Ser Cys Tyr Gln Leu Met Ile Thr Ala Gly Ile Phe Leu
    210                 215                 220

Gly Tyr Cys Thr Asn Tyr Gly Thr Lys Ser Tyr Ser Asn Ser Val Gln
225                 230                 235                 240

Trp Arg Val Pro Leu Gly Leu Cys Phe Ala Trp Ser Leu Phe Met Ile
                245                 250                 255

Gly Ala Leu Thr Leu Val Pro Glu Ser Pro Arg Tyr Leu Cys Glu Val
            260                 265                 270

Asn Lys Val Glu Asp Ala Lys Leu Ser Ile Ala Lys Ser Asn Lys Val
        275                 280                 285

Ser Pro Glu Asp Pro Ala Val Gln Ala Glu Leu Asp Leu Ile Met Ala
    290                 295                 300

Gly Ile Glu Ala Glu Lys Leu Ala Gly Asn Ala Ser Trp Gly Glu Leu
305                 310                 315                 320

Phe Ser Thr Lys Thr Lys Val Phe Gln Arg Leu Leu Met Gly Val Phe
                325                 330                 335

Val Gln Met Phe Gln Gln Leu Thr Gly Asn Asn Tyr Phe Phe Tyr Tyr
            340                 345                 350

Gly Thr Val Ile Phe Lys Ser Val Gly Leu Asp Asp Ser Phe Glu Thr
        355                 360                 365
```

```
Ser Ile Val Ile Gly Val Val Asn Phe Ala Ser Thr Phe Phe Ser Leu
    370                 375                 380

Trp Thr Val Glu Asn Leu Gly Arg Arg Lys Cys Leu Leu Leu Gly Ala
385                 390                 395                 400

Ala Thr Met Met Ala Cys Met Val Ile Tyr Ala Ser Val Gly Val Thr
                405                 410                 415

Arg Leu Tyr Pro His Gly Lys Ser Gln Pro Ser Ser Lys Gly Ala Gly
            420                 425                 430

Asn Cys Met Ile Val Phe Thr Cys Phe Tyr Ile Phe Cys Tyr Ala Thr
                435                 440                 445

Thr Trp Ala Pro Val Ala Trp Val Ile Thr Ala Glu Ser Phe Pro Leu
450                 455                 460

Arg Val Lys Ser Lys Cys Met Ala Leu Ala Ser Ala Ser Asn Trp Val
465                 470                 475                 480

Trp Gly Phe Leu Ile Ala Phe Phe Thr Pro Phe Ile Thr Ser Ala Ile
                485                 490                 495

Asn Phe Tyr Tyr Gly Tyr Val Phe Met Gly Cys Leu Val Ala Met Phe
                500                 505                 510

Phe Tyr Val Phe Phe Val Pro Glu Thr Lys Gly Leu Ser Leu Glu
            515                 520                 525

Glu Ile Gln Glu Leu Trp Glu Glu Gly Val Leu Pro Trp Lys Ser Glu
530                 535                 540

Gly Trp Ile Pro Ser Ser Arg Arg Gly Asn Asn Tyr Asp Leu Glu Asp
545                 550                 555                 560

Leu Gln His Asp Asp Lys Pro Trp Tyr Lys Ala Met Leu Glu
            565                 570

<210> SEQ ID NO 2
<211> LENGTH: 32
<212> TYPE: DNA
<213> ORGANISM: Artificial Sequence
<220> FEATURE:
<223> OTHER INFORMATION: Primer

<400> SEQUENCE: 2
ggtgccggta actgtatcat tgtctttacc tg                              32

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
acaggtaaag acaatgatac agttaccggc acc                             33

<210> SEQ ID NO 4
<211> LENGTH: 59
<212> TYPE: DNA
<213> ORGANISM: Artificial Sequence
<220> FEATURE:
<223> OTHER INFORMATION: Primer

<400> SEQUENCE: 4
aacacaaaaa caaaaagttt ttttaatttt aatcaaaaaa tggcagttga ggagaacaa   59

<210> SEQ ID NO 5
<211> LENGTH: 60
<212> TYPE: DNA
```

<213> ORGANISM: Artificial Sequence
<220> FEATURE:
<223> OTHER INFORMATION: Primer

<400> SEQUENCE: 5
gaatgtaagc gtgacataac taattacatg actcgagtta ttctagcatg gccttgtacc    60

<210> SEQ ID NO 6
<211> LENGTH: 38
<212> TYPE: DNA
<213> ORGANISM: Artificial Sequence
<220> FEATURE:
<223> OTHER INFORMATION: Primer

<400> SEQUENCE: 6
gtcattggtg tagtctactt tgcctccact ttctttag                            38

<210> SEQ ID NO 7
<211> LENGTH: 38
<212> TYPE: DNA
<213> ORGANISM: Artificial Sequence
<220> FEATURE:
<223> OTHER INFORMATION: Primer

<400> SEQUENCE: 7
gaaagtggag gcaaagtaga ctacaccaat gacaatgg                            38

<210> SEQ ID NO 8
<211> LENGTH: 38
<212> TYPE: DNA
<213> ORGANISM: Artificial Sequence
<220> FEATURE:
<223> OTHER INFORMATION: Primer

<400> SEQUENCE: 8 ttatttttc tactacggtg ccgttatttt caagtcag                             38

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
gacttgaaaa taacggcacc gtagtagaaa aaataattg                           39

<210> SEQ ID NO 10
<211> LENGTH: 36
<212> TYPE: DNA
<213> ORGANISM: Artificial Sequence
<220> FEATURE:
<223> OTHER INFORMATION: Primer

<400> SEQUENCE: 10
gtctgaatat gttaccattt ccttgctttg tttgtg                              36

<210> SEQ ID NO 11
<211> LENGTH: 36
<212> TYPE: DNA
<213> ORGANISM: Artificial Sequence
<220> FEATURE:
<223> OTHER INFORMATION: Primer

<400> SEQUENCE: 11
aaacaaagca aggaaatggt aacatattca gacatg                              36

```
<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
ttgagaaggt ttggtaagaa acataaggat ggtacc                              36

<210> SEQ ID NO 13
<211> LENGTH: 41
<212> TYPE: DNA
<213> ORGANISM: Artificial Sequence
<220> FEATURE:
<223> OTHER INFORMATION: Primer

<400> SEQUENCE: 13
accatcctta tgtttcttac caaaccttct caaaaagtct g                        41

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
agctattcga actcacttca atggagagtt ccattagg                            38

<210> SEQ ID NO 15
<211> LENGTH: 38
<212> TYPE: DNA
<213> ORGANISM: Artificial Sequence
<220> FEATURE:
<223> OTHER INFORMATION: Primer

<400> SEQUENCE: 15
tggaactctc cattgaagtg agttcgaata gctctttg                            38

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
ggtaataatt acgattcaga ggatttacaa catgacg                             37

<210> SEQ ID NO 17
<211> LENGTH: 38
<212> TYPE: DNA
<213> ORGANISM: Artificial Sequence
<220> FEATURE:
<223> OTHER INFORMATION: Primer

<400> SEQUENCE: 17
atgttgtaaa tcctctgaat cgtaattatt acctcttc                            38
```

VARIANTS OF GAL2 TRANSPORTER AND THEIR USES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 510110_401USPC_SEQUENCE_LISTING.txt. The text file is 8 KB, was created on Apr. 18, 2017, and is being submitted electronically via EFS-Web.

The present invention relates to polypeptides which are Gal2 variants comprising at least one amino acid substitution at a position corresponding to M435, and optionally further amino acid substitution(s). The present invention further relates to nucleic acid molecules encoding the polypeptides and to host cells containing said nucleic acid molecules. The present invention further relates to a method for the production of bioethanol and/or other bio-based compounds, comprising the expression of said nucleic acid molecules, preferably in said host cells. The present invention also relates to the use of the polypeptides, nucleic acids molecule or host cells for the production of bioethanol and/or other bio-based compounds, and/or for the recombinant fermentation of biomaterial containing pentose(s), preferably D-xylose and/or L-arabinose.

BACKGROUND OF THE INVENTION

The beer, wine and baking yeast *Saccharomyces cerevisiae* has already been used for centuries for the production of bread, wine and beer owing to its characteristic of fermenting sugar to ethanol and carbon dioxide. In biotechnology, *S. cerevisiae* is used particularly in ethanol production for industrial purposes, in addition to the production of heterologous proteins. Ethanol is used in numerous branches of industry as an initial substrate for syntheses. Ethanol is gaining increasing importance as an alternative fuel, due to the increasingly scarce presence of oil, the rising oil prices and continuously increasing need for petrol worldwide. Moreover, *S. cerevisiae* is also used for the production of other biofuels or valuable biochemical compounds like isobutanol, succinic acid, farnesen/farnesan or artemisinin.

In order to make possible a favourably-priced and efficient biofuel production, the use of biomass containing lignocellulose, such as for example straw, waste from the timber industry and agriculture and the organic component of everyday household waste, presents itself as an initial substrate. Firstly, said biomass is very convenient and secondly is present in large quantities. The three major components of lignocellulose are lignin, cellulose and hemicellulose. Hemicellulose, which is the second most frequently occurring polymer after cellulose, is a highly branched heteropolymer. It consists of pentoses (L-arabinose, D-xylose), uronic acids (4-O-methyl-D-glucuronic acid, D-galacturonic acid) and hexoses (D-mannose, D-galactose, L-rhamnose, D-glucose). Although hemicellulose can be hydrolyzed more easily than cellulose, it contains the pentoses L-arabinose and D-xylose, which can normally not be converted by the yeast *S. cerevisae*.

In order to be able to use pentoses for fermentations, these must firstly enter the cell through the plasma membrane. Although *S. cerevisiae* is not able to metabolize D-xylose or L-arabinose, it can take up D-xylose or L-arabinose into the cell. However, *S. cerevisiae* does not have a specific transporter. The transport takes place by means of the hexose transporters. The affinity of the transporters to D-xylose is, however, distinctly lower than to D-glucose (Kotter and Ciriacy, 1993). In yeasts which are able to metabolize D-xylose, such as for example *P. stipitis, C. shehatae* or *P. tannophilus* (Du Preez et al., 1986), there are both unspecific low-affinity transporters, which transport D-glucose, and also specific high-affinity proton symporters only for D-xylose (Hahn-Hagerdal et al., 2001).

In earlier experiments, some yeasts were found, such as for example *Candida tropicalis, Pachysolen tannophilus, Pichia stipitis, Candida shehatae*, which by nature ferment D-xylose or L-arabinose or can at least assimilate it. However, these yeasts lack entirely the capability of fermenting L-arabinose and D-xylose to ethanol, or they only have a very low ethanol yield (Dien et al., 1996). Moreover, very little is yet known about the uptake of D-xylose and L-arabinose. In the yeast *C. shehatae* one assumes a proton symport (Lucas and Uden, 1986). In *S. cerevisiae*, it is known from the galactose permease Gal2 that it can transport D-xylose but also transports L-arabinose, which is very similar in structure to D-galactose. (Kou et al., 1970). Most hexose transporters can mediate uptake of D-xylose.

Alcoholic fermentation of pentoses in biotechnologically modified yeast strains of *S. cerevisiae*, wherein inter alia various genes of the yeast strain *Pichia stipitis* were used for the genetic modification of *S. cerevisiae*, was described in recent years particularly in connection with the fermentation of xylose. The engineering concentrated here particularly on the introduction of the genes for the initial xylose assimilation from *Pichia stipitis*, a xylose-fermenting yeast, into *S. cerevisiae*, i.e. into a yeast which is traditionally used in the ethanol production from hexose (Jin et al. 2004).

Jeppson et al. (2006) describe xylose fermentation by *S. cerevisiae* by means of the introduction of a xylose metabolic pathway which is either similar to that in the yeasts *Pichia stipitis* and *Candida shehatae*, which naturally use xylose, or is similar to the bacterial metabolic pathway.

Katahira et al. (2006) describe sulphuric acid hydrolysates of lignocellulose biomass such as wood chips, as an important material for the production of fuel bioethanol. In this study, a recombinant yeast strain was constructed, which is able to ferment xylose and cellooligosaccharides. For this, various genes were integrated into this yeast strain and namely for the inter-cellular expression of xylose reductase and xylitol dehydrogenase from *Pichia stipitis* and xylulokinase from *S. cerevisiae* and for the presentation of beta-glucosidase from *Aspergillus acleatus* on the cell surface. In the fermentation of sulphuric acid hydrolysates of wood chips, xylose and cellooligosaccharides were fully fermented by the recombinant strain after 36 hours.

Pitkanen et al. (2005) describe the obtaining and characterizing of xylose chemostat isolates of a *S. cerevisiae* strain, which over-expresses genes of *Pichia stipitis* coding for xylose reductase and xylitol dehydrogenase and the gene which codes endogenous xylulokinase. The isolates were obtained from aerobic chemostat cultures on xylose as the single or major carbon source. Under aerobic conditions on minimal medium with 30 g/l xylose, the growth rate of the chemostat isolates was 3 times higher than that of the original strain (0.15 $h^{-1}$ compared with 0.05 $h^{-1}$). The xylose uptake rate was increased almost two-fold. The activities of the key enzymes of the pentose phosphate metabolic pathway (transketolase, transaldolase) were increased two-fold, whilst the concentrations of their substrates (pentose-5-phosphates, sedoheptulose-7-phosphate) were lowered accordingly.

Brat et al. (2009) screened nucleic acid databases for sequences encoding putative xylose isomerases and finally were able to clone and successfully express a highly active new kind of xylose isomerase from the anaerobic bacterium *Clostridium phytofermentans* in *S. cerevisiae*. Heterologous expression of this enzyme confers on the yeast cells the ability to metabolize D-xylose and to use it as the sole carbon and energy source.

Demeke et al. (2013) developed an expression cassette containing 13 genes including *C. phytofermentans* xylA, encoding D-xylose isomerase, and enzymes of the pentose phosphate pathway and inserted the cassette in two copies in the genome of the industrial *S. cerevisiae* strain Ethanol Red. Subsequent EMS mutagenesis, genome shuffling and selection in D-xylose-enriched lignocellulose hydrolysate, followed by multiple rounds of evolutionary engineering in complex medium with D-xylose, gradually established highly efficient D-xylose fermentation.

Becker and Boles (2003) describe the engineering and the selection of a laboratory strain of *S. cerevisiae* which is able to use L-arabinose for growth and for fermenting it to ethanol. This was possible due to the over-expression of a bacterial L-arabinose metabolic pathway, consisting of *Bacillus subtilis* AraA and *Escherichia coli* AraB and AraD and simultaneous over-expression of yeast galactose permease transporting L-arabinose in the yeast strain.

Molecular analysis of the selected strain showed that the predetermining precondition for a use of L-arabinose is a lower activity of L-ribulokinase. However, inter alia, a very slow growth is reported from this yeast strain.

Wiedemann and Boles (2008) show that expressing of the codon-optimized genes of L-arabinose isomerase from *Bacillus licheniformis* and L-ribulokinase and L-ribulose-5-P 4-epimerase from *Escherichia coli* strongly improved L-arabinose conversion rates.

Farwick et al. (2014) developed a new system for screening and engineering of pentose transporters which are no longer inhibited by glucose. This system was based on a D-xylose-fermenting yeast strain having deletions of all hexose-transporters and all hexo-/glucokinases (hxt$^0$ hxk$^0$ strain). D-glucose can no longer be used as a carbon source but interferes with D-xylose utilization at transport level. As a result, mutant transporters that allow D-xylose uptake in the presence of increasing concentrations of D-glucose could easily be selected.

Using this system in evolutionary engineering and mutagenesis approaches the authors were able to generate specific D-xylose transporters from *S. cerevisiae* hexose transporters. Some of these mutant transporters had an exchange at a position corresponding to N376 of the galactose transporter Gal2. However, although they proved resistant against glucose most of them had a reduced uptake rate for xylose.

WO 2008/080505 A1 discloses an arabinose transporter from *Pichia stipitis*, which enables yeast cells to take up L-arabinose. EP 11 001 841.3 discloses a specific arabinose transporter of the plant *Arabidopsis thaliana* for the construction of pentose-fermenting yeasts. WO 2012/049170 A2 and WO 2012/049173 A1 disclose pentose and glucose fermenting yeast cells which contain and express among other nucleic acids, a polypeptide with arabinose permease activity comprising a mutation in position T219 to asparagine or N376 to serine of Gal2 which renders the transporter resistant against the inhibitory effect of glucose.

There still exists a need in the art for specific pentose transporters, in particular specific D-xylose transporters, which have a higher affinity and/or higher activity for pentoses, in particular combined with glucose resistance, which allow to specifically take up D-xylose and/or L-arabinose into cells, such as yeast cells, with high uptake rates even at low pentose concentrations, and therefore to promote the utilization and fermentation of pentoses, in particular D-xylose and/or L-arabinose, and in particular in the simultaneous presence of glucose.

It is thus an object of the present invention to provide improved and/or more specific transporters, which transport pentose(s), such as D-xylose and/or L-arabinose with higher activities and/or higher affinities.

SUMMARY OF THE INVENTION

According to the present invention this object is solved by a polypeptide, comprising at least one amino acid substitution at a position corresponding to M435 of the amino acid sequence of SEQ ID NO: 1,
wherein the polypeptide has at least 60%, or preferably at least 70% or 80% or 90% or 95% sequence identity with the amino acid sequence of SEQ ID NO: 1, and wherein the polypeptide has an in vitro and/or in vivo pentose transport function.

According to the present invention this object is solved by a nucleic acid molecule coding for a polypeptide of the present invention.

According to the present invention this object is solved by a host cell, containing a nucleic acid molecule of the present invention and preferably expressing said nucleic acid molecule, wherein said host cell is preferably a fungus cell and more preferably a yeast cell, such as *Saccharomyces* species, *Kluyveromyces* sp., *Hansenula* sp., *Pichia* sp. or *Yarrowia* sp.

According to the present invention this object is solved by a method for the production of bioethanol and/or other bio-based compounds, comprising the expression of a nucleic acid molecule according to the present invention, preferably in a host cell according to the present invention.

According to the present invention this object is solved by using a polypeptide according to the present invention, a nucleic acid molecule according to the present invention, or a host cell according to the present invention for the production of bioethanol and/or other bio-based compounds, and/or for the recombinant fermentation of biomaterial containing pentose(s), preferably D-xylose and/or L-arabinose.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Gal2 Variants

As discussed above, the present invention provides Gal2 variants.

In particular, the present invention provides a polypeptide, comprising at least one amino acid substitution at a position corresponding to M435 of the amino acid sequence of SEQ ID NO: 1.

The polypeptide of the present invention has at least 60%, or preferably at least 70% or 80% or 90% or 95% sequence identity with the amino acid sequence of SEQ ID NO: 1, and has an in vitro and/or in vivo pentose transport function.

Preferably, the polypeptide of the present invention is Gal2 of *Saccharomyces cerevisiae*.

SEQ ID NO: 1 is the wild-type protein or amino acid sequence of Gal2 of CEN.PK2-1C and CEN.PK113-7D.

Gal2 of CEN.PK2-1C is a protein of 574 amino acids. http://www.yeastgenome.org/cgi-bin/FUNGI/getSeq.pl?seq=YLR081W_CEN.PK113-7D The polypeptides, preferably the Gal2 variants, according to the invention comprise at least one amino acid substitution at a position corresponding to M435 of the amino acid sequence of SEQ ID NO: 1 or of an amino acid sequence, which is at least 60% identical, preferably at least 70% identical, more preferably at least 80% identical, even more preferably at least 90% identical, yet more preferably 95% identical, and yet more preferably 99% identical to the amino acid sequence of SEQ ID NO: 1.

As used herein, the term "at a position corresponding to" means the respective position in SEQ ID No: 1 which, however, in related polypeptide chains can have another relative position number. The equivalent substitution can be determined by comparing a position in both sequences, which may be aligned for the purpose of comparison. The relative position of the amino acid can vary due to different length of the related polypeptide, or deletions or additions of amino acids in the related polypeptide.

The polypeptides, preferably the Gal2 variants, according to the invention have an in vitro and/or in vivo pentose transport function, in particular an in vitro and/or in vivo D-xylose and/or L-arabinose transport function.

Preferably, the pentose is D-xylose and/or L-arabinose.

As used herein, if not otherwise indicated, the term "xylose" means the same as D-xylose, "arabinose" means the same as L-arabinose, and "glucose" means the same as D-glucose.

As used herein, the term "percent (%) identical" refers to sequence identity between two amino acid sequences. Identity can be determined by comparing a position in both sequences, which may be aligned for the purpose of comparison. When an equivalent position in the compared sequences is occupied by the same amino acid, the molecules are considered to be identical at that position.

As used herein, the term "functional equivalent" refers to amino acid sequences that are not 100% identical to the amino acid sequence of SEQ ID NO. 1 and comprise amino acid additions and/or insertions and/or deletions and/or substitutions and/or exchanges, which do not alter or change the activity or function of the protein as compared to the protein having the amino acid sequence of SEQ ID NO: 1, i.e. an "functional equivalent", for example, encompasses an amino acid sequence with conservative amino acid substitutions or smaller deletions and/or insertions as long as these modifications do not substantially affect the in vitro and/or in vivo L-arabinose transport function.

Generally, a person skilled in the art is aware of the fact that some amino acid exchanges in the amino acid sequence of a protein do not have an influence on the (secondary or tertiary) structure, function and/or activity of that protein. Amino acid sequences with such "neutral" amino acid exchanges as compared to the amino acid sequences disclosed herein fall within the scope of the present invention.

In a preferred embodiment, the polypeptides, preferably the Gal2 variants, according to the present invention, comprising at least one amino acid substitution at a position corresponding to M435 of SEQ ID NO. 1, comprise the amino acid substitution M435I.

Preferably, the amino acid substitution at a position corresponding to M435 increase(s) the activity of the in vitro and/or in vivo pentose transport function compared to the polypeptide without such amino acid substitution(s).

Preferably, the amino acid substitution at a position corresponding to M435 increase(s) the affinity of the polypeptide for pentose(s) compared to the polypeptide without such amino acid substitution(s).

Further Amino Acid Substitution(s)

In one embodiment, the polypeptides, preferably the Gal2 variants, according to the present invention comprise further amino acid substitution(s):
preferably an amino acid substitution at a position corresponding to N376 of the amino acid sequence of SEQ ID NO: 1.

Said further amino acid substitution(s) are preferably selected from N376Y or N376F.

The present invention preferably provides the following polypeptides/Gal2 variants:
M435I
M435I/N376Y
M435I/N376F
M435I/T354A
M435I/V71I
M435I/T354A/V71I
M435I/T354A/N376Y
M435I/T354A/N376F
M435I/T354A/N376Y/V71I
M435I/T354A/N376F/V71I Nucleic Acid Molecules As discussed above, the present invention provides a nucleic acid molecule, coding for a polypeptide according to the present invention.

In one embodiment, the nucleic acid molecule of the present invention further comprises:
vector nucleic acid sequences, preferably expression vector sequences, and/or
promoter nucleic acid sequences and terminator nucleic acid sequences, and/or
comprises other regulatory nucleic acid sequence.

In one embodiment, the nucleic acid molecule of the present invention comprises dsDNA, ssDNA, PNA, CNA, RNA or mRNA or combinations thereof.

The nucleic acid molecules according to the invention preferably comprise nucleic acid sequences, which are (except for the addition of the amino acid substitution(s) according to the invention) identical with the naturally occurring nucleic acid sequence or are codon-optimized for the use in a host cell.

The nucleic acid molecule used according to the present invention is preferably a nucleic acid expression construct.

Nucleic acid expression constructs according to the invention are expression cassettes comprising a nucleic acid molecule according to the invention, or expression vectors comprising a nucleic acid molecule according to the invention or an expression cassette, for example.

A nucleic acid expression construct preferably comprises regulatory sequences, such as promoter and terminator sequences, which are operatively linked with the nucleic acid sequence coding for the polypeptide(s) of the invention.

The nucleic acid expression construct may further comprise 5' and/or 3' recognition sequences and/or selection markers.

Host Cells

As discussed above, the present invention provides host cells containing a nucleic acid molecule according to the present invention.

Preferably, the host cells of the present invention express said nucleic acid molecule.

Preferably, a host cell according to the present invention is a fungus cell and more preferably a yeast cell.

The yeast cell is preferably a member of a genus selected from the group of *Saccharomyces* species, *Kluyveromyces* sp., *Hansenula* sp., *Pichia* sp. or *Yarrowia* sp.

The yeast cell is more preferably a member of a species selected from the group of *S. cerevisiae, S. bulderi, S. barnetti, S. exiguus, S. uvarum, S. diastaticus, K. lactis, K. marxianus, K. fragilis, H. polymorpha, P. pastoris* and *Y. lipolytica*, such as *S. cerevisiae, K. lactis, H. polymorpha, P. pastoris* or *Y. lipolytica*.

In a preferred embodiment, the host cell belongs to the species *Saccharomyces cerevisiae*.

When the nucleic acid molecule/sequence coding for the polypeptide (preferably Gal2 variant(s)) of the present invention is expressed in a host cell (preferably a yeast cell), the host cell is imparted the capability to take up D-xylose and/or L-arabinose, which then may be metabolized further. Through this, the cell is able to grow on D-xylose and/or L-arabinose as a carbon source.

Preferably, the host cell (preferably yeast cell) has an increased uptake rate for D-xylose and/or L-arabinose compared to a cell not containing a nucleic acid molecule according to the present invention.

In a preferred embodiment, the host cell (preferably yeast cell) of the present invention further contains
  nucleic acid molecules which code for proteins of a xylose metabolic pathway (preferably xylose isomerase and xylulokinase), and/or
  nucleic acid molecules which code for proteins of an arabinose metabolic pathway (preferably arabinose isomerase, ribulokinase, ribulose-5-P 4-epimerase).
  Such a host cell has preferably
  an increased D-xylose and/or L-arabinose utilization rate and/or
  a faster growth rate with D-xylose and/or L-arabinose compared to a cell not containing a nucleic acid molecule according to the present invention.

For example, the host cell (preferably yeast cell) of the present invention can further contain nucleic acid molecules which code for proteins of an arabinose metabolic pathway, in particular for arabinose isomerase, ribulokinase, ribulose-5-P 4-epimerase.

Preferred are proteins of the bacterial arabinose metabolic pathway, in particular *E. coli* araB L-ribulokinase, *E. coli* araD L-ribulose-5-P 4-epimerase and *B. licheniformis* araA L-arabinose-isomerase.

In a preferred embodiment, a host cell (preferably yeast cell) according to this invention is modified by the introduction and expression of the genes araA (L-arabinose-isomerase), araB (L-ribulokinase) and araD (L-ribulose-5-P-4-epimerase) and in addition over-expresses a TAL1 (transaldolase) gene, as described for example by the inventors in EP 1 499 708 B1, and in addition to this contains at least one nucleic acid molecule according to the invention.

Depending on the intended use of the yeast cell, said yeast cell can contain, express or overexpress further nucleic acid sequences coding for further proteins, such as transaldolase TAL1 and/or TAL2, transketolase TKL1 and/or TKL2, D-ribulose-5-phosphate 3-epimerase RPE1, ribose-5-phosphate ketol-isomerase RKI1 or the corresponding sequences from other organisms encoding the same enzyme activities.

For example, the host cell (preferably yeast cell) of the present invention can further overexpress nucleic acid molecules which code for proteins of a xylose metabolic pathway, in particular for xylose isomerase and xylulokinase.

Preferred is *Clostridium phytofermentans* or *Piromyces* xylA xylose isomerase and *S. cerevisiae* XKS1 xylulokinase.

In a preferred embodiment, a host cell (preferably yeast cell) according to this invention is modified by the introduction and/or overexpression of the genes xylA (xyloseisomerase), XKS1 (xylulokinase) and in addition over-expresses a TAL1 (transaldolase) gene.

Depending on the intended use of the yeast cell, said yeast cell can contain, express or overexpress further nucleic acid sequences coding for further proteins, such as transaldolase TAL1 and/or TAL2, transketolase TKL1 and/or TKL2, D-ribulose-5-phosphate 3-epimerase RPE1, ribose-5-phosphate ketol-isomerase RKI1 or the corresponding sequences from other organisms encoding the same enzyme activities.

Methods and Uses for Producing Bioethanol

As discussed above, the present invention provides a method for the production of bioethanol and/or other bio-based compounds.

Said method comprises the expression of a nucleic acid molecule according to the present invention, preferably in a host cell according to the present invention.

As discussed above, the present invention provides the use of
  a polypeptide according to the present invention,
  a nucleic acid molecule according to the present invention, or
  a host cell according to the present invention,
for the production of bioethanol and/or other bio-based compounds,
and/or for the recombinant fermentation of biomaterial containing pentose(s), preferably D-xylose and/or L-arabinose.

The term "bio-based compounds" or "other bio-based compounds" as used herein refers to chemical compounds and substances, which are obtained from biological materials and raw materials (biomass), particularly by using microorganisms.

The (other) bio-based compounds can be compounds, which are selected from, but not limited to:
lactic acid, acetic acid, succinic acid, malic acid or other organic acids,
1-butanol, isobutanol, 2-butanol, other alcohols,
amino acids, alkanes, terpenes, isoprenoids, solvents, pharmaceutical compounds, vitamins.

Further Description of Preferred Embodiments

The inventors have identified Gal2 variants which exhibit
  increased activity of the in vitro and/or in vivo pentose transport function and/or
  increased affinity for pentose(s)
compared to the wildtype or to a Gal2 polypeptide without the respective amino acid substitution(s).

The inventors have, thus, identified Gal2 variants which, thus, confer a host cell (preferably a yeast cell) the capability to take up D-xylose and/or D-arabinose and, preferably, the capability for an increased uptake for pentose(s), preferably D-xylose and/or D-arabinose.

For this, reference is also to be made to the examples and figures.

Uptake of L-Arabinose and D-Xylose

So that pentose(s), in particular, D-xylose and/or L-arabinose, can be metabolized by S. cerevisiae, they must firstly be taken up by the cell.

All hexose transporters tested for the pentose D-xylose have a much higher affinity to hexoses than to D-xylose. For L-arabinose, a similar situation is assumed. Of all strains constructed hitherto, which can utilize pentoses (D-xylose or L-arabinose), a relatively slow growth is reported. Above all, the slow and poor uptake of the pentoses is named as a reason for this (Becker and Boles, 2003; Richard et al., 2002). In fermentations in a sugar mixture, consisting of D-glucose and D-xylose or D-glucose and L-arabinose, the sugars are not converted simultaneously. Due to the high affinity of the transporters for D-glucose, D-glucose is metabolized at first. A so-called diauxic shift occurs. Only after the D-glucose is exhausted is the pentose converted in a second, distinctly slower growth phase (Kuyper et al., 2005a; Kuyper et al., 2005b). The absence of specific transporters for pentoses is given as an explanation.

Gal2

The hexose galactose is transported by the high affinity transporter Gal2 ($K_m$=1 to 5 mM) which is equally affine for glucose ($K_m$=1.5 to 1.9) (see e.g. Reifenberger et al., 1997). Like the other structural genes needed for galactose utilization (GAL), galactose kinase; GAL10, mutarotase/UDP-glucose-4-epimerase; GAL7, galactose-1-phosphate uridyl transferase), its expression is repressed in the presence of glucose and also needs the induction by galactose. Gal2 is also target of catabolite inactivation (Horak and Wolf, 1997). Gal2 is one of only few transporters which can transport L-arabinose. Like most of the other hexose transporters it can transport D-xylose. However, its affinity for L-arabinose and D-xylose is quite low. Therefore, at low D-xylose or L-arabinose concentrations the uptake activity is very low.

Farwick et al. (2014) developed mutant transporters that allow D-xylose uptake in the presence of D-glucose. Some of these mutant transporters had an amino acid exchange at a position corresponding to N376 of the galactose transporter Gal2. However, although they proved resistant against glucose most of them had a reduced uptake rate for xylose.

The polypeptides of the present invention exhibit an increased uptake rate and/or affinity for xylose, in particular in combination with mutations which make them resistant against inhibition by glucose.

Various mutagenesis methods had to be used as well as evolutionary engineering under very specific conditions with engineered yeast strains with a variety of different modifications, to find improved Gal2 derived pentose transporters. These transporters had to be tested in elaborate screening systems, with growth tests and sugar uptake assays. Finally, the mutant transporters had to be sequenced and from a variety of mutations those had to be elucidated which finally were responsible for the improved properties.

D-xylose accounts for up to 35% of total sugars in xylan-rich lignocellulosic biomass such as hard woods and straw (see Demeke et al. 2013). Biomass with significant amounts of arabinose (source of the data: U.S. Department of Energy http://www.eere.energy.gov/biomass/progs/search1.cgi):

| Type of biomass | L-arabinose [%] |
| --- | --- |
| Switchgrass | 3.66 |
| Large *bothriochloa* | 3.55 |
| Tall fescue | 3.19 |
| *Robinia* | 3 |
| Corn stover | 2.69 |

-continued

| Type of biomass | L-arabinose [%] |
| --- | --- |
| Wheat straw | 2.35 |
| Sugar can bagasse | 2.06 |
| Chinese *lespedeza* | 1.75 |
| *Sorghum bicolor* | 1.65 |

The Gal2 variants according to the invention are also of great importance for its utilization.

Possibilities for use of a functional and at the same time specific pentose transporter in the yeast S. cerevisiae are firstly the production from lignocellulosic hydrolysates of bioethanol and the production of high-grade precursor products for further chemical syntheses, particularly when pentose concentrations are low and in the simultaneous presence of glucose.

The following list originates from the study "Top Value Added Chemicals From Biomass" (see www1.eere.energy.gov/biomass/pdfs/35523.pdf). Here, 30 chemicals were categorized as being particularly valuable, which can be produced from biomass.

| Number of C atoms | Top 30 Candidates |
| --- | --- |
| 1 | hydrogen, carbon monoxide |
| 2 | |
| 3 | glycerol, 3-hydroxypropionic acid, lactic acid, malonic acid, propionic acid, serine |
| 4 | acetoin, asparaginic acid, fumaric acid, 3-hydroxybutyrolactone, malic acid, succinic acid, threonin |
| 5 | arabitol, furfural, glutamic acid, itaconic acid, levulinic acid, proline, xylitol, xylonic acid |
| 6 | aconitic acid, citrate, 2,5-furandicarboxylic acid, glucaric acid, lysine, levoglucosan, sorbitol |

As soon as these chemicals are produced from lignocelluloses by bioconversion (e.g. fermentations with yeasts), it is important to have specific, highly active transporter(s) for the hemicellulose sugars arabinose and xylose.

The following examples and drawings illustrate the present invention without, however, limiting the same thereto.

The transformants were cultivated in 5 ml SCM-ura with 20 g/l maltose at 30°, washed with water and adjusted to an $OD_{600}$ of 1. Thereof it followed a serial dilution. 5 µl were dropped onto the respective media and it was incubated for three days at 30°. As a control for the dilution SCM-ura with 20 g/l maltose was taken. The cells of the mutated transporters were dropped onto SCD-ura with 0.2% and 2% glucose, as well as SCG-ura with 0.2% and 2% D-galactose to test their functionality. Furthermore the wild type, Gal2_ep3.1 and Gal2_N376Y were used for comparison.

Figure 2:
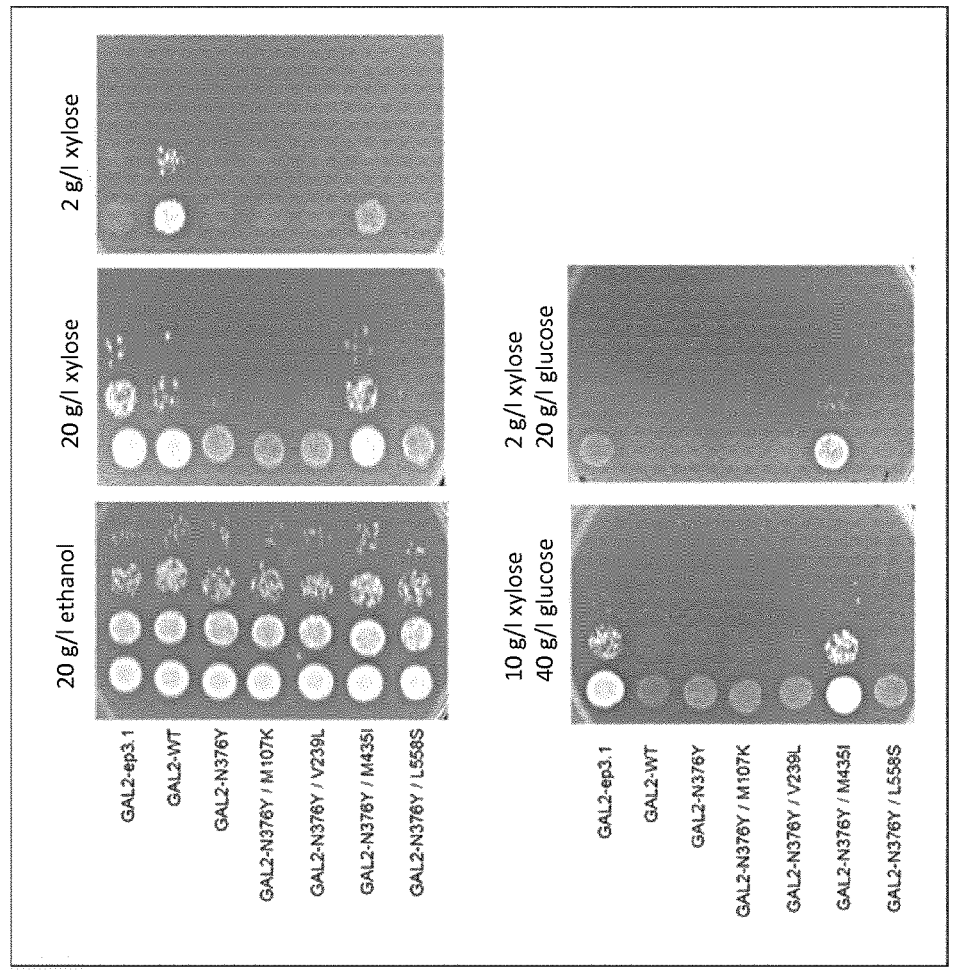

FIG. 2: Growth test of Gal2_ep3.1 mutants in comparison to N376Y in AFY10

The transformants were cultivated in 5 ml SCE-ura-leu with 2% ethanol at 30°, washed with water and adjusted to an $OD_{600}$ of 1. Thereof it followed a serial dilution. 5 µl were dropped onto the respective media and it was incubated for five days at 30°. As a control for the dilution SCE-ura-leu with 2% ethanol was taken. The cells of the mutated transporters were dropped onto SCX-ura-leu with 0.2% and 2% D-xylose, as well as SC-ura-leu with 1% D-xylose with 4% D-glucose and SC-ura-leu with 0.2% D-xylose and 2% D-glucose to test their functionality. Furthermore the wild type and Gal2_ep3.1 were used for comparison.

Figure 3:
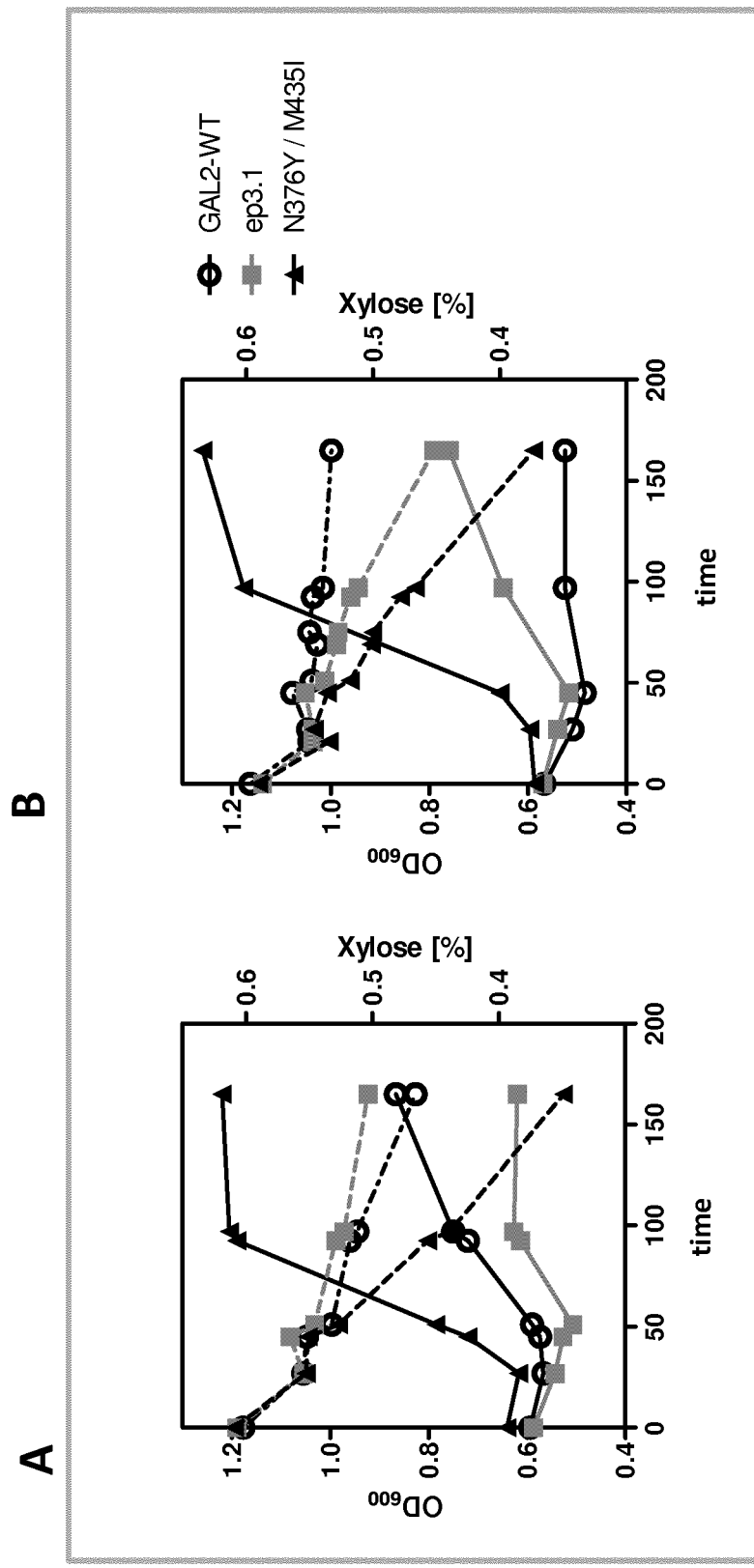

FIG. 3: Growth test in liquid media and fermentation

The strain AFY10, which was transformed with YEp181_pHXT7-opt.XI_Clos and p426H7-GAL2_wt (WT) or p426H7-GAL2_ep3.1 (ep3.1) or p426-GAL2_N376Y+M435I (M435I), was incubated in 150 ml SCE-ura-leu+G418. This was the preculture which was used to start the fermentation with an $OD_{600}$ of 0.6 in 30 ml SC-ura-leu with 0.6% xylose (A) or with 0.6% xylose with 2% glucose (B). The cultures were incubated at 180 rpm and 30° for seven days. Samples were taken for growth measurements as well as metabolite analysis. The measurements of the showed xylose concentration was done with HPLC whereas the samples were diluted 1:5. The entire xylose concentration of the supernatant is showed in % (w/v). The data indicate the averages of three independent replicates whereby the error bars are not shown for reason of clarity.

Figure 4:
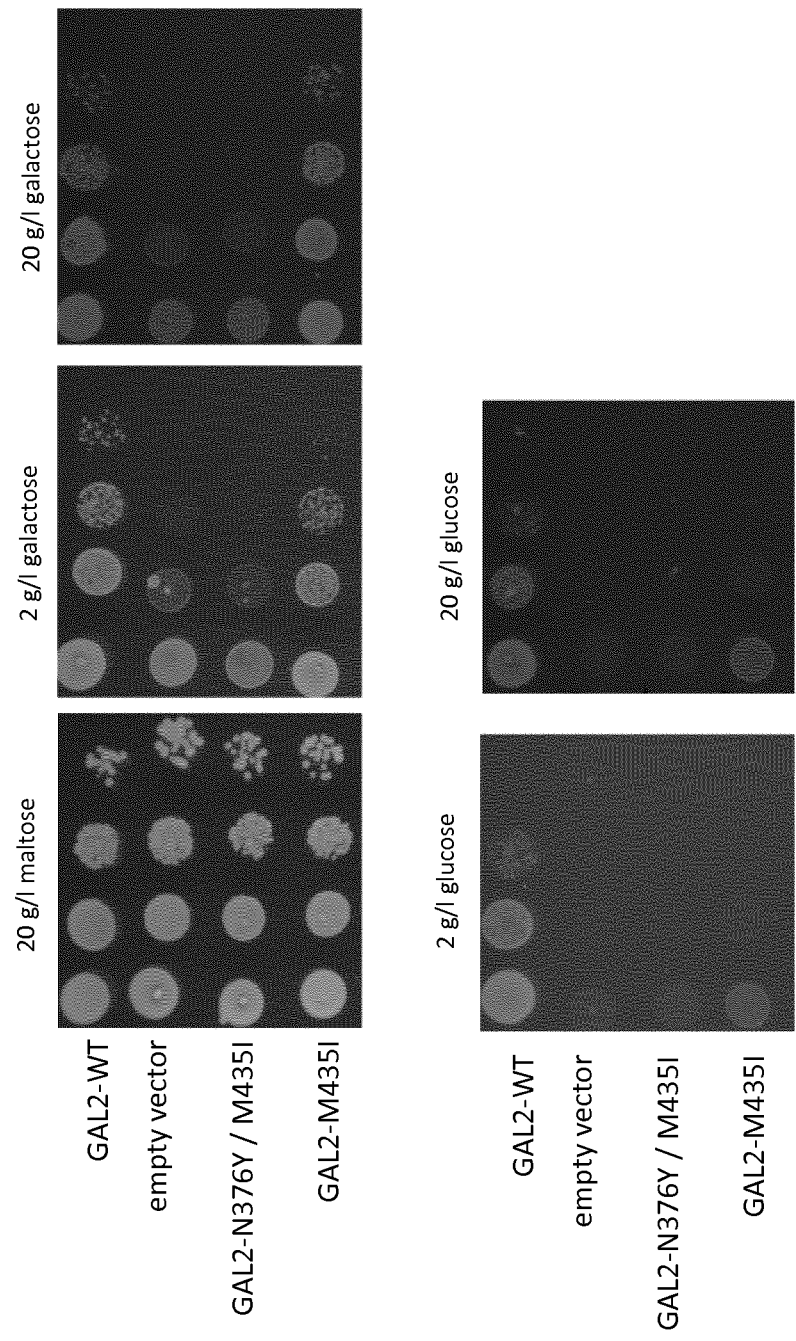

FIG. 4: Drop test of Gal2_M435I in EBY.VW4000 after three days at 30°. Several dilutions from left to right were dropped (undiluted, 1:10, 1:100, 1:1000).

Figure 5:
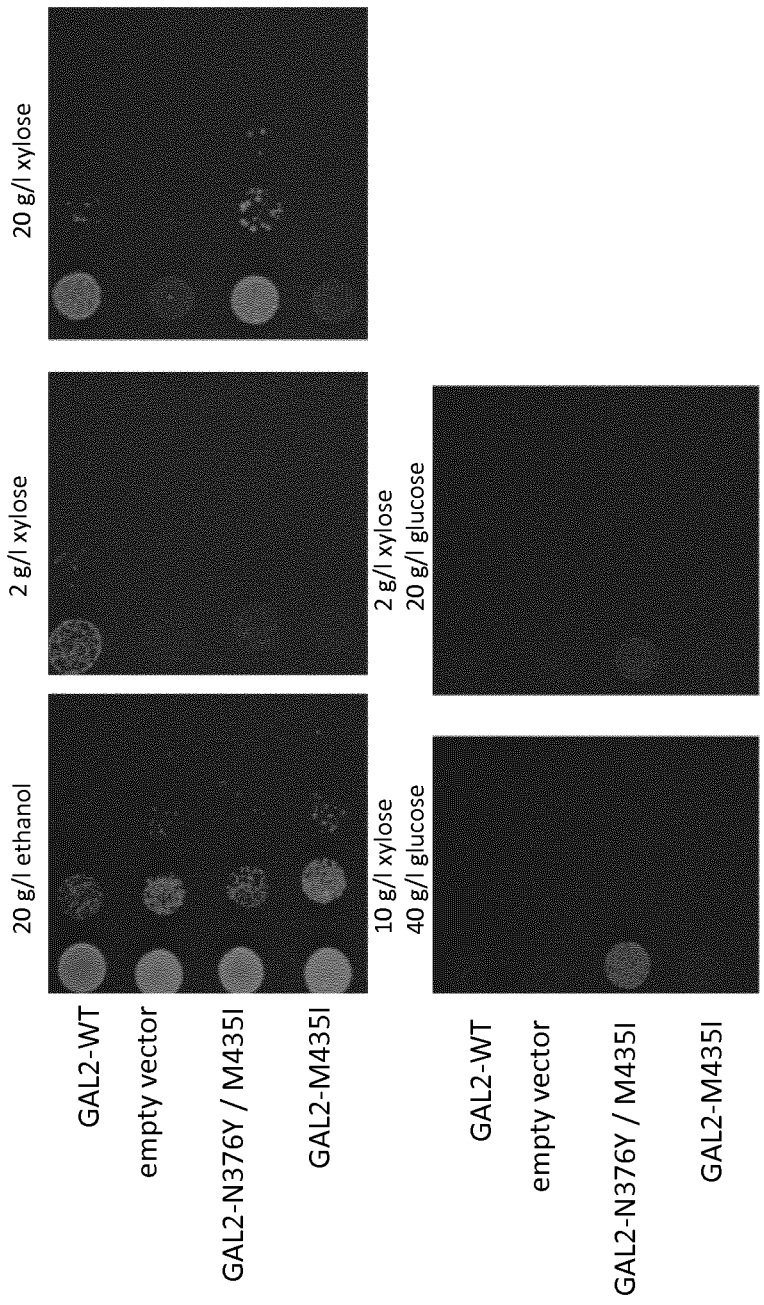

FIG. 5: Drop test of Gal2_M435I in AFY10 after five days at 30°. Several dilutions were dropped from left to right (undiluted, 1:10, 1:100, 1:1000).

Figure 6:
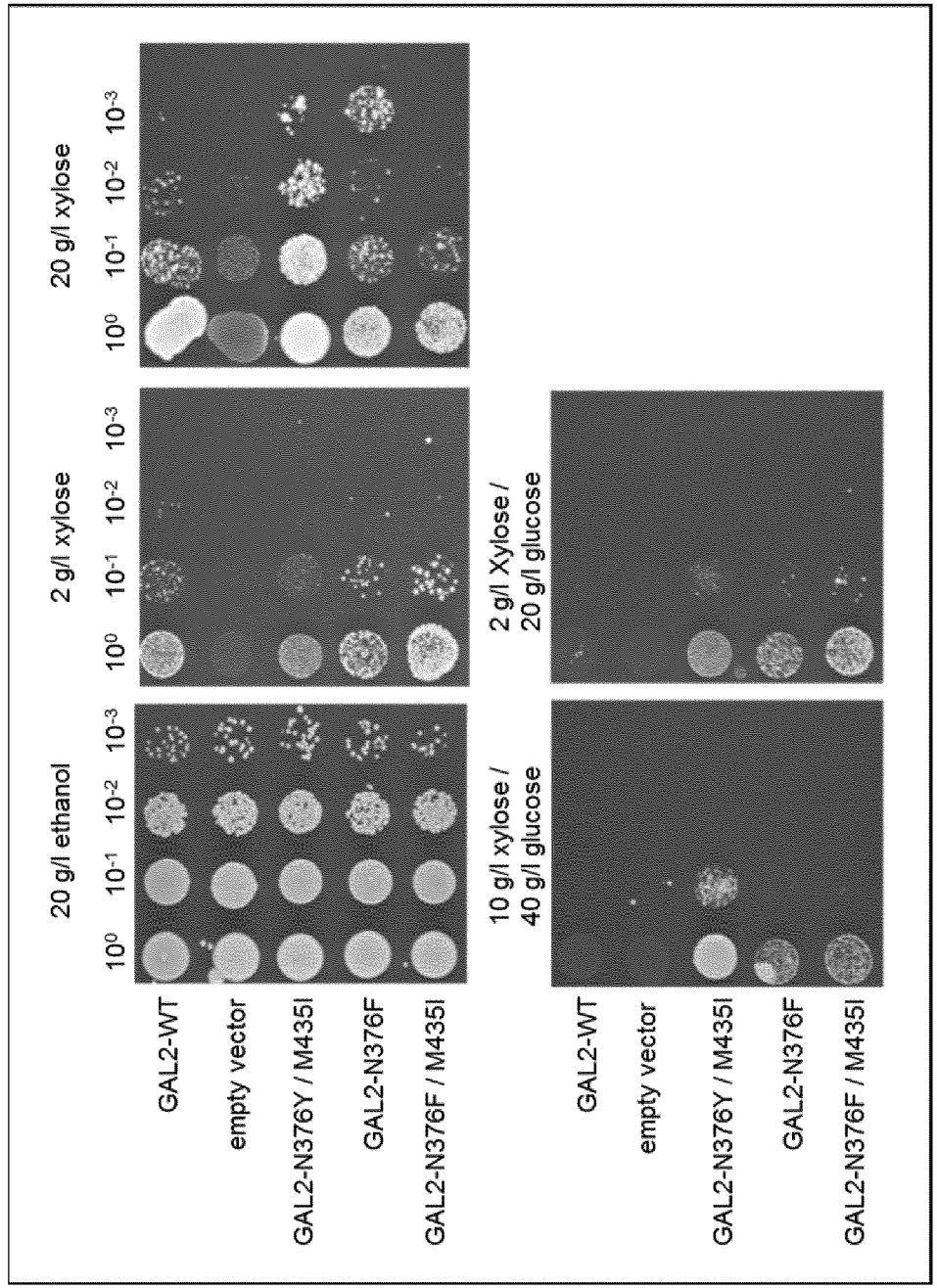

FIG. 6: Drop test of Gal2_N376F, N376F+M435I and N376Y+M435I in AFY10 after five days at 30°. Several dilutions were dropped from left to right (undiluted, 1:10, 1:100, 1:1000). But on 20 g/l xylose the order was different (undiluted, 1:100, 1:1000, 1:10).

Figure 7:
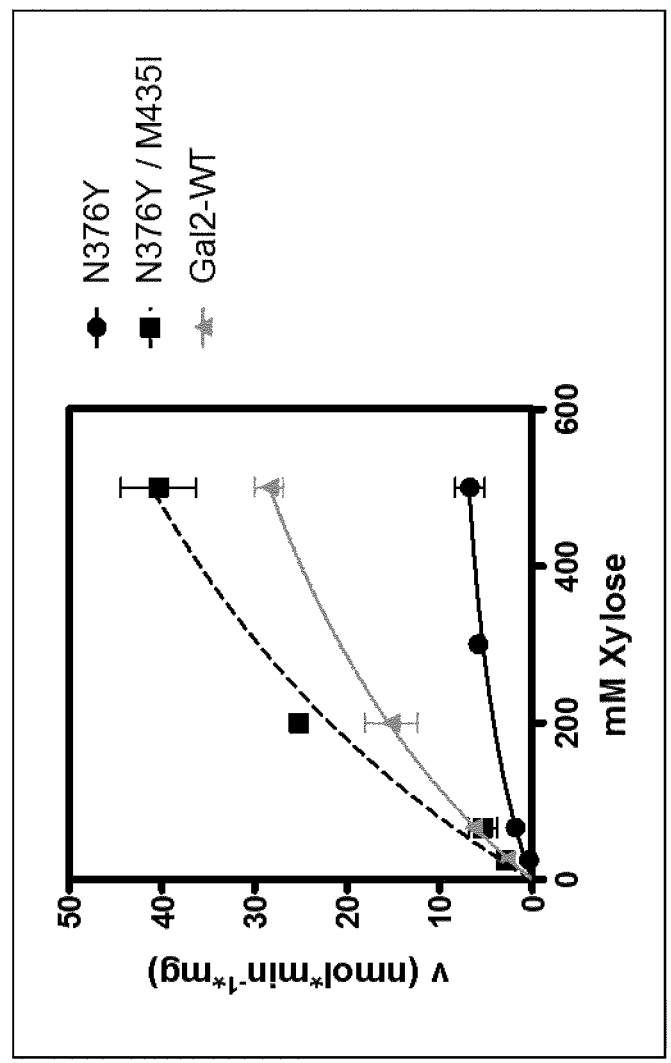

FIG. 7: Xylose uptake assay of Gal2_N376Y, N376Y+M435I and Gal2 wild type in EBY.VW4000 (three independent replicates). The uptake velocity is shown in nmol xylose per minute per milligram cell dry mass.

Figure 8:
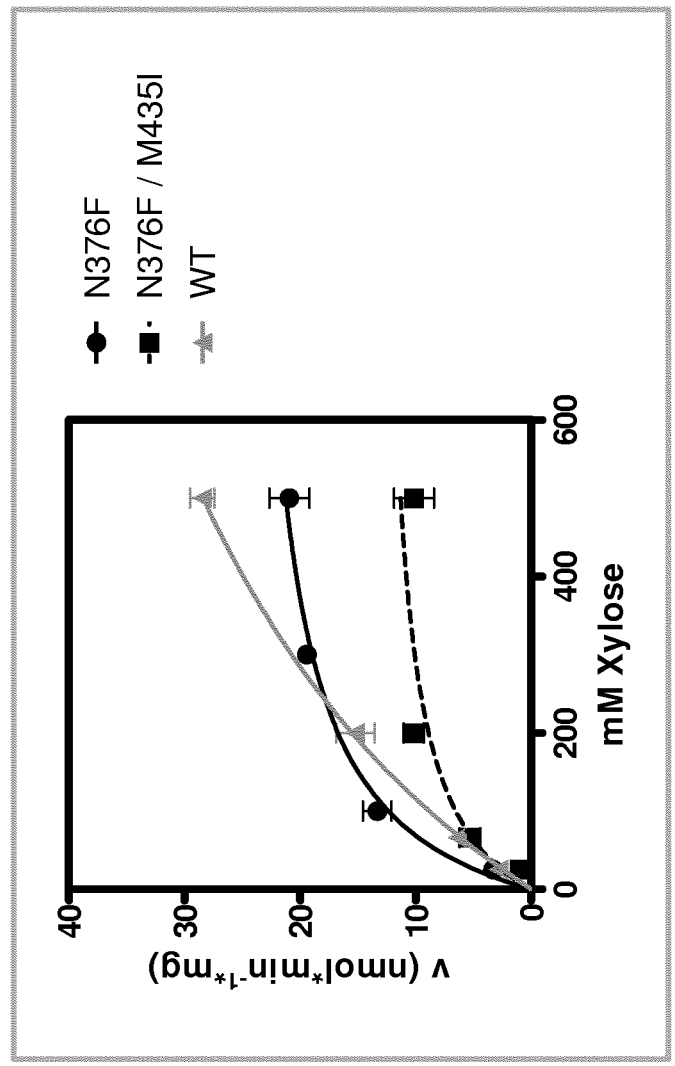

FIG. 8: Xylose uptake assay of Gal2_N376F, N376F+M435I and Gal2 wild type in EBY.VW4000 (three independent replicates). The uptake velocity is shown in nmol xylose per minute per milligram cell dray mass.

EXAMPLES

Methods
Strains and Media
Bacteria
E. coli SURE (Stratagene)
Full medium LB 1% trypton, 0.5% yeast extract, 0.5% NaCl, pH 7.5 (see Sambrook and Russell, 2001)
For selection on a plasmid-coded antibiotic resistance, 40 µg/ml ampicillin was added to the medium after autoclaving. Solid culture media additionally contained 1.9% agar. The culture took place at 37° C.
Yeast
CEN.PK2-1C
MATa leu2-3,112 ura3-52 trp1-289 his3-Δ1 MAL2-8$^c$ SUC2 (EUROSCARF, Frankfurt)
Strain EBY.VW4000
EBY.VW4000 (Genotype: MATa leu2-3,112ura3-52 trp1-289 his3-Δ1 MAL2-8c SUC2 Δhxt1-17Δgal2 stlΔ::loxP agt1 Δ::loxP mph2Δ::loxP mph3Δ::loxP) (Wieczorke et al., 1999)
Strain Ethanol Red
available from Lesaffre, Lille, France. Described in Demeke et al. (2013).
Strain HDY.GUF10
Xylose and arabinose consuming industrial S. cerevisiae strain derived from Ethanol Red (Dietz 2013).

Strain AFY10
EBY.VW4000 glk1Δ::loxP hxk1Δ::loxP hxk2Δ::loxP ylr446wΔ::loxP pyk2Δ::pPGK1-opt.XKS1-tPGK1 pTPI1-TAL1-tTAL1 pTDH3-TKL1-tTKL1 pPFK1-RPE1-tRPE1 pFBA-RKI1-tRKI1 loxP (Farwick et al., 2014).
Strain AFY10X
AFY10+YEp-kanR_optXI (Farwick et al., 2014).
Synthetic Complete Selective Medium SC
0.67% yeast nitrogen base w/o amino acids and ammonium sulphate, 0.5% ammonium sulphate, 20 mM potassium dihydrogenphosphate, pH 6.3, amino acid/nucleobase solution without the corresponding amino acids for the auxotrophy markers of the plasmids used, carbon source in the respectively indicated concentration Concentration of the amino acids and nucleobases in the synthetic complete medium (Zimmermann, 1975): adenine (0.08 mM), arginine (0.22 mM), histidine (0.25 mM), isoleucine (0.44 mM), leucine (0.44 mM), lysin (0.35 mM), methionine (0.26 mM), phenylalanine (0.29 mM), threonine (0.48 mM), tryptophan (0.19 mM), tyrosin (0.34 mM), uracil (0.44 mM) and valine (0.49 mM). As carbon sources, L-arabinose, D-glucose, D-galactose, D-mannose, ethanol and maltose were used, as indicated.

Solid full and selective media contained in addition 1.9% agar. The culture of the yeast cells took place at 30° C.

| Plasmids | |
|---|---|
| Plasmid | Referenz |
| p426H7 | Becker and Boles, 2003 |
| YEp181_pHXT7-optXI_Clos | Subtil and Boles, 2012 |
| p426H7_GAL2_WT | |
| p426H7_GAL2_ep3.1 | |
| p426H7-GAL2_EtOHred | |
| p426H7-GAL2_GUF10 | |
| p426H7-GAL2_N376Y | |
| p426H7-GAL2_N376Y + M107K | |
| p426H7-GAL2_N376Y + V239L | |
| p426H7-GAL2_N376Y + M435I | |
| p426H7-GAL2_N376Y + M558S | |
| p426H7_GAL2-M435I | |
| p426H7_GAL2-N376F | |
| p426H7_GAL2-N376F + M435I | |

Preparation of DNA
Isolation of Plasmid DNA from E. coli
Small-scale preparations of plasmid DNA from E. coli cultures were done using the GeneJET™ Plasmid Miniprep Kit (Fisher Scientific) according to manufacturer's instructions. The QUIAGEN Plasmid Maxi Kit was used for large scale preparations.
Isolation of Plasmid and Genomic DNA from S. cerevisiae
For isolation of genomic and plasmid DNA from yeast cells 5-10 ml of stationary phase cultures were harvested by centrifugation (1 min, 2000×g) and washed once in 1 ml sterile ddH$_2$O. The cell pellet was resuspended in 400 µl YP-buffer 1 by vortexing and then lysed by addition of 400 µl YP-buffer 2, ⅓ to ⅔ Vol glass beads (Ø 0.25-0.5 mm) and 8 minutes of shaking on a VXR basic Vibrax (IKA) at 2000 rpm. Cell debris was pelleted by centrifugation (30 sec, 16000×g) and 650 µl of the supernatant transferred to a fresh eppendorf tube. 325 µl of cold YP-buffer 3 were added and the sample was vortexed and then incubated on ice for 10 minutes for precipitation of proteins and other contaminants. The sample was centrifuged (10-15 min, 4° C., 16000×g), 700 µl of the supernatant were transferred to a fresh eppendorf tube and 700 µl isopropanol were added. After mixing vigorously, the sample was incubated for 10 minutes at RT to allow precipitation of the DNA, which was then pelleted by centrifugation (≥30 min, RT, 16000×g). The DNA-pellet was washed twice with 500 µl of cold (−20° C.) 70% (v/v) ethanol, with centrifugation steps of 5 minutes at RT and 16000×g, then dried at RT for 10 minutes and dissolved in 15-30 µl sterile ddH2O depending on the size of the DNA pellet.

Determining the DNA Concentration

The DNA concentration is measured by spectral photometry in a wavelength range of 240-300 nm. If the purity of the DNA, determined by the quotient E260 nm/E280 nm is 1.8, then the extinction E260 nm=1.0 corresponds to a DNA concentration of 50 µg dsDNA/ml (Sambrook and Russell, 2001).

DNA Purification of PCR Products

The purification of the PCR products took place with the "QIAquick PCR Purification Kit" of the company Qiagen, according to the manufacturer's information.

Digestion of DNA with Restriction Endonucleases (Restriction Digestion)

For the site-specific cleavage of DNA restriction endonucleases from New England Biolabs (NEB) or Fermentas were used with the provided buffers and according to the instructions of the manufacturer. Usually 1-3 units per µg DNA were used for the reaction, which was incubated for 2-12 hours. This method was used to prepare vectors for recombinational cloning, to confirm correctly assembled plasmids or to specifically degrade a certain plasmid from a mixture.

Polymerase Chain Reaction (PCR)

Different polymerases were used for different PCR experiments in this work. For confirmation of genomic gene deletion or integration the Crimson Taq polymerase (NEB) was used. For amplification of ORFs (for sequencing), genes for recombinational cloning or amplification of integrative cassettes for genomic gene deletion or integration the Phusion or Q5 polymerases (NEB) were used. Composition of PCR reactions and the corresponding PCR program are displayed in the Tables below. Annealing temperatures of primer pairs were calculated with the $T_m$ calculator tool on the NEB homepage. All PCRs were performed in a Mastercycler gradient (Eppendorf), Piko Thermo Cycler (Finnzymes) or Progene PCR cycler (Techne).

| Composition of PCR reactions with Crimson Taq polymerase | | | |
|---|---|---|---|
| component | 15 µl reaction | 25 µl reaction | final concentration |
| 5x Crimson Taq reaction buffer | 3 µl | 5 µl | 1x |
| 2 mM dNTP mix | 1.5 µl | 2.5 µl | 200 µM each |
| 10 µM primer (each) | 0.3 | 0.5 µl | 0.2 µM each |
| template DNA | variable | variable | variable |
| Crimson Taq DNA polymerase | 0.15 µl | 0.25 µl | 0.025 U/µl |
| nuclease-free water | to 15 µl | to 25 µl | |

| PCR program for reactions with Crimson Taq polymerase | | |
|---|---|---|
| step | temperature (° C.) | time |
| initial denaturation | 95 | 1 min |
| 30-35 cycles | 95 | 22 sec |
| | 45-68 | 35 sec |
| | 68 | 1 min/kb |
| final extension | 68 | 5 min |
| hold | 4-10 | |

| Composition of PCR reactions with Phusion or Q5 polymerase | | | |
|---|---|---|---|
| component | 25 µl reaction | 50 µl reaction | final conc. |
| 5x Phusion HF/Q5 reaction buffer | 5 µl | 10 µl | 1x |
| 2 mM dNTPs mix | 2.5 µl | 5 µl | 200 µM each |
| 10 µM primer (each) | 0.5 µl | 1 µl | 200 µM each |
| template DNA | variable | variable | variable |
| Phusion/Q5 High-Fidelity DNA polymerase | 0.25 µl | 0.5 µl | 0.02 U/µl |
| nuclease-free water | to 25 µl | to 50 µl | |

| PCR program for reactions with Phusion or Q5 polymerase | | |
|---|---|---|
| step | temperature (° C.) | time |
| initial denaturation | 98° C. | 1 min |
| 15-35 cycles | 98° C. | 10 sec |
| | 50-72° C. | 20 sec |
| | 72° C. | 15 sec/kb (for plasmids) |
| | | 30 sec/kb (for gDNA) |
| final extension | 72° C. | 5 min |
| hold | 4-10° C. | |

Fusion PCR

A fusion PCR was used for construction the ORF of HXT7-N370F for recombinational cloning. In the first step two overlapping fragments of HXT7 were amplified in two separate Q5 PCR reactions with p426H7_HXT7 as a template. The PCR reactions were separated in a 1.5% agarose gel and the correct fragments purified from the corresponding gel pieces. Equal molar amount of both fragments (20 ng minimum) were used in a Q5 PCR reaction without primers. This PCR reaction was run for 6 cycles, before 1 µl of forward and reverse primer (from 10 µM stocks) were added. The reaction was then run for another 20 cycles.

Error-Prone PCR (epPCR)

For generation of random mutagenized ORFs of GAL2 the GeneMorph II Random Mutagenesis Kit (Agilent Technologies) was applied. The manufacturer's protocol has been followed. The PCR reaction has been run for 33 cycles. The amount of template DNA has been varied to achieve different mutation rates (see Table below) The analysis of epPCR-products revealed that the desired amplification specifications have been met. The PCR fragments were purified and used as templates for a Phusion PCR reaction to extend the fragments' ends with homologous overhangs.

| Amount of template DNA used in different epPCRs and | | | |
|---|---|---|---|
| | amount of template | amplification | |
| mutation rate | (acceptable range) | desired | found |
| medium (4.5-9 mut/kb) | 205 ng (100-500 ng) | 10-100 | ≈45 |
| high (9-16 mut/kb) | 23 ng (0.1-100 ng) | 100-10000 | ≈250 |

Agarose Gel-Electrophoresis for DNA or RNA Separation

Fragments in DNA or RNA samples were separated by size using agarose gels with concentrations ranging from 0.7 to 2.0% (w/v) agarose (Sambrook and Russell, 2001). 1× TAE-buffer was used for preparation of gels and as running buffer. The GeneRuler 1 kb DNA Ladder (Fisher Scientific) was used for sizing of the DNA fragments. DNA samples were mixed with ⅕ Vol of 6×DNA loading dye before loading onto the gel. RNA samples were mixed with the same volume 2×RNA loading dye, incubated at 96° C. for 10 min and stored on ice prior to loading. Gels were run at up to 6-10 V/cm for 30 to 45 minutes depending on current, gel percentage and expected fragment sizes. DNA and RNA were visualized by UV-light (254 nm) after incubation of the gel in an ethidium bromide bath.

DNA-Purification and DNA-Extraction from Agarose Gels

To purify DNA (e.g. from PCR reactions or after restriction digestions) and to extract DNA from agarose gels the NucleoSpin® Extract II-Kit (Macherey-Nagel) was used according to manufacturer's instructions.

DNA Sequencing

Sequencing of DNA samples was done by GATC Biotech AG (Konstanz, Germany). The samples contained 30-100 ng/µl (plasmids) or 10-50 ng/µl (PCR products) of DNA. Suitable primers (10 µM) were sent to GATC Biotech together with the DNA sample.

Transformation of E. coli

E. coli cells were transformed by electroporation according to the protocol of Dower (Dower et al., 1988) and Wirth (Wirth, 1989) using a Bio-Rad Gene Pulser. DNA (from E. coli or yeast DNA preparations) was added to the frozen competent E. coli cells and the sample was incubated and thawed for 10 min on ice. The cell suspension was then transferred to electroporation cuvettes and directly pulsed. The Bio-Rad Gene Pulser was set to a voltage of 2.5 kV per cm, a resistance of 200Ω and a capacity of 25 µF. Immediately after the pulse the cells were mixed with 1 ml of pre-warmed SOC medium and transferred to an eppendorf tube. The cells were incubated at 37° C. for 45 min at 600-800 rpm in a Thermomixer (Eppendorf) before plating on selective LB agar plates containing kanamycin or ampicillin. In case the cells were transformed with a HXT7-coding plasmid, the incubation was performed at room temperature for 4 hours without shaking or at 20-25° C. with shaking for 2 hours.

Transformation of S. cerevisiae

For transformation of S. cerevisiae, two different protocols of the LiAc/SS carrier DNA/PEG method from Gietz et al. (Gietz and Schiestl, 2007a, Gietz and Schiestl, 2007b) were used with small deviations. Liquid cultures were grown in suitable medium to an OD of 0.6-1.0. Centrifugation of the culture and for the washing steps were shortened to 2 minutes at 3000×g. The single-stranded carrier DNA was used as a 10 mg/ml solution, allowing a volume of 54 µl or 74 µl of DNA in the transformation mix, respectively. The duration of the heat-shock was 35 minutes. After transformation the whole cell suspension was directly plated on the selection medium or, in case of transformations with a dominant selection marker, transferred to 5 ml of appropriate liquid medium for regeneration. After regeneration cells were pelleted, resuspended in 50-100 µl medium and plated out.

DNA amounts for transformations were approx. 500 ng for single plasmids, ≥1000 ng each for co-transformations with multiple plasmids and ≥2000 ng and more for integrative DNA-cassettes (e.g. for gene deletions).

Codon Optimization of Genes

The ORF of some genes has been codon-optimized. The codons have been adapted to the codon-usage of S. cerevisiae as determined by the preferred codons of the glycolytic genes. Described in Wiedemann et al. (Wiedemann and Boles, 2008).

Plasmid Construction by Homologous Recombination (Recombinational Cloning)

Plasmids were constructed in vivo by homologous recombination of suitable DNA fragments (vector backbone and insert(s)) in S. cerevisiae. For this purpose the respective vector was linearized at the site of insertion by restriction digestion. Optionally, the resulting vector backbone was purified by agarose gel-electrophoresis and subsequent gel extraction. The inserts were designed to have flanking sequences (>30 bp) homologous to the region targeted for insertion or, in case of multiple insert fragments, to each other. Inserts were amplified by PCR and could be provided with homologous sequences by using primers with corresponding 5' ends (homologous overhangs). S. cerevisiae was transformed with the DNA fragments and transformants were plated out on selective medium. Colonies were picked to inoculate selective liquid medium. DNA was isolated from these cultures and used for transformation of E. coli for plasmid separation and proliferation. Plasmids containing the gyrase inhibitor gene ccdB are toxic to most E. coli strains so ccdB-resistant strain E. coli DB3.1 was used for these plasmids. Plasmids were isolated from E. coli single-colony cultures and verified by analytic restriction digestion and DNA sequencing. Glycerol stock cultures were set up for correct clones.

Genomic Gene Deletion or Insertion by Homologous Recombination

For gene deletions in the genome of S. cerevisiae, marker cassettes were integrated into the respective gene by homologous recombination (Carter and Delneri, 2010, Gilldener et al., 1996, Sauer, 1987). The marker cassettes were amplified by PCR using primers with 5' ends homologous to the target gene to enable site-directed insertion. The cassettes are composed of a dominant marker gene (kanMX4/G418, hphNT1/Hygromycin B, natNT2/clonNAT), flanked by a promoter (pTEF) and a terminator (tTEF, tCYC1 and tADH1, respectively) and loxP sites. These sites allow excision of the genome-integrated marker cassettes by the cre recombinase, which clears the marker for another round of gene deletion. After transformation of S. cerevisiae with a deletion cassette, cells were plated out on selective medium and replica plated on the same medium once. Single colonies were streaked out again to obtain single clones, which were then picked and grown in selective medium. The DNA was isolated from these cultures and the correct integration was confirmed by PCR with different primer combinations. Primers for confirmation are termed as seen in the Table below. Glycerol stock cultures were set up for correct clones.

| \multicolumn{3}{c}{Nomenclature of primers used for confirmation of genomic integration by PCR} | | |
|---|---|---|
| name | position | direction |
| A1 | upstream of the integration site | downstream |
| A2 | within the region that gets replaced by the integration | upstream |
| A3 | within the region that gets replaced by the integration | downstream |
| A4 | downstream of the integration site | upstream |

| Nomenclature of primers used for confirmation of genomic integration by PCR | | |
|---|---|---|
| name | position | direction |
| K2 | within the deletion cassette/gene that is integrated | upstream |
| K3 | within the deletion cassette/gene that is integrated | downstream |

For recycling of the marker, cells were transformed with a plasmid encoding the cre recombinase under control of the galactose-inducible GALJ-promotor (pSH47 or pNatCre). After brief induction of the recombinase, cells were selected for loss of the dominant marker by replica plating. Since full expression of the recombinase is lethal in hxt⁰ strains, basal expression of the recombinase under non-inducing conditions was used for these strains. Removal of the cassette was again controlled by PCR (see above). The integration of gene cassettes for overexpression of genes was done accordingly. Within these cassettes only the dominant marker is flanked by loxP sites and is excised, the rest of the cassette remains in the genome.

| List of primers | | |
|---|---|---|
| Primer name | Sequence (5'-3') [SEQ ID NO.] | Description |
| Gal2_M435I_fw | GGTGCCGGTAACTGT ATCATTGTCTTTACC TG [SEQ ID NO. 2] | forward primer for mutagenesis of M435 to I in GAL2 |
| Gal2_M435I_rev | ACAGGTAAAGACAAT GATACAGTTACCGGC ACC [SEQ ID NO. 3] | reverse primer for mutagenesis of M435 to I in GAL2 |
| GAL2_for | AACACAAAAACAAAA AGTTTTTTAATTTT AATCAAAAAATGGCA GTTGAGGAGAACAA [SEQ ID NO. 4] | forward primer for GAL2 amplification |
| GAL2_rev | GAATGTAAGCGTGAC ATAACTAATTACATG ACTCGAGTTATTCTA GCATGGCCTTGTACC [SEQ ID NO. 5] | reverse primer for GAL2 amplification |
| Gal2_N376Y_fw | GTCATTGGTGTAGTC TACTTTGCCTCCACT TTCTTTAG [SEQ ID NO. 6] | forward primer for mutagenesis of N376 to Y in GAL2 |
| Gal2_N376Y_rev | GAAAGTGGAGGCAAA GTAGACTACACCAAT GACAATGG [SEQ ID NO. 7] | reverse primer for mutagenesis of N376 to Y in GAL2 |
| GAL2 T354A fw | TTATTTTTTCTACTA CGGTGCCGTTATTTT CAAGTCAG [SEQ ID NO. 8] | forward primer for mutagenesis of T354 to A in GAL2 |
| GAL2 T354A rv | GACTTGAAAATAACG GCACCGTAGTAGAAA AAATAATTG [SEQ ID NO. 9] | reverse primer for mutagenesis of T354 to A in GAL2 |
| GAL2 V71I fw | GTCTGAATATGTTAC CATTTCCTTGCTTTG TTTGT [SEQ ID NO. 10] | forward primer for mutagenesis of V71 to I in GAL2 |

| List of primers | | |
|---|---|---|
| Primer name | Sequence (5'-3') [SEQ ID NO.] | Description |
| GAL2 V71I rv | AAACAAAGCAAGGAA ATGGTAACATATTCA GACATG [SEQ ID NO. 11] | reverse primer for mutagenesis of V71 to I in GAL2 |
| GAL2-M107K_fw | TTGAGAAGGTTTGGT AAGAAACATAAGGAT GGTACC [SEQ ID NO. 12] | forward primer for mutagenesis of M107 to K in GAL2 |
| GAL2-M107K_rev | ACCATCCTTATGTTT CTTACCAAACCTTCT CAAAAAGTCTG [SEQ ID NO. 13] | reverse primer for mutagenesis of M107 to K in GAL2 |
| GAL2_V239L_fw | AGCTATTCGAACTCA CTTCAATGGAGAGTT CCATTAGG [SEQ ID NO. 14] | forward primer for mutagenesis of V239 to L in GAL2 |
| GAL2_V239L_rev | TGGAACTCTCCATTG AAGTGAGTTCGAATA GCTCTTTG [SEQ ID NO. 15] | reverse primer for mutagenesis of V239 to L in GAL2 |
| GAL2_L558S_fw | GGTAATAATTACGAT TCAGAGGATTTACAA CATGACG [SEQ ID NO. 16] | forward primer for mutagenesis of L558 to S in GAL2 |
| GAL2_L558S_rev | ATGTTGTAAATCCTC TGAATCGTAATTATT ACCTCTTC [SEQ ID NO. 17] | reverse primer for mutagenesis of L558 to S in GAL2 |

Methods for Cell Cultivation and Fermentation Experiments

Spectrophotometrical Determination of Cell Density

The cell concentration in a liquid culture was quantified spectrophotometrically by measuring the optical density at 600 nm ($OD_{600}$). Samples of the cell culture or dilutions thereof were placed in a polystyrene (PS) cuvette and analysed in a Ultrospec 2100 pro spectrophotometer (GE Healthcare, USA) at 600 nm.

Glycerol Stock Cultures

For long time storage of specific strains and plasmid-containing E. coli glycerol stock cultures were prepared. For this purpose stationary cultures of S. cerevisiae or growing cultures of E. coli were mixed 1:1 with 50% (v/v) glycerol and stored at −80° C.

Semi-Solid Agar Cultivation

The Semi-solid agar method of cultivation was chosen to expand the plasmid cDNA library (in E. coli). By this method representational biases that can occur during growth in liquid culture can be minimized. Incubation is done at 30° C. helping to stabilize unstable clones (Hanahan et al., 1991, Sassone-Corsi, 1991). The protocol can be found at Life technologies website. In brief, 2× concentrated LB medium is mixed with 3 g/l SeaPrep agarose while stirring, autoclaved and cooled down to 37° C. The antibiotic and $4·10^5$ to $6·10^5$ (per 450 ml medium) are added to the medium and mixed for 2 minutes. The bottles are then incubated in an ice-bath at 0° C. for 1 hour and then gently transferred to 30° C. for 40-45 h of incubation (without disturbance). After growth the cells can be pelleted from the semi-solid agar by centrifugation at 10400×g.

Serial Dilution Spot Assays (Drop Tests)

For easy comparison of growth of different S. cerevisiae strains under various growth conditions a serial dilution spot assay was performed. Cells were grown in liquid culture to exponential phase in appropriate medium, collected by centrifugation (2000×g, 2 min), washed twice with sterile water and then resuspended to an $OD_{600}$ of 1.0 in selective medium without carbon source. From this cell suspension a ten-fold serial dilution was prepared in selective medium (four dilution steps). 6 µl of each cell suspension were spotted on plates of the media to be examined and allowed to dry. Plates were incubated at 30° C.

Aerobic Batch Fermentations

Aerobic batch fermentations were done in shake flasks of varying sizes (volume 5-10× of the culture volume) on rotary shakers (150-180 rpm) usually at 30° C. The evolutionary engineering was done as a serial aerobic batch fermentation (details see below)

Anaerobic Batch Fermentations

For anaerobic batch fermentations, shake flasks were sealed with a rubber plug and a fermentation lock. The volume of the flasks was matching the culture volume of 100 ml. The cultures were stirred continuously with 120 rpm on a magnetic stirrer at 30° C. In this work the fermentations were done at $OD_{600}=10$. For this purpose grown cells were harvested and set to an $OD_{600}$ of 20 in 50 ml fermentation medium without carbon source. To start the experiment this cell suspension was added to the prepared flasks containing 50 ml fermentation medium supplemented with 2× concentrated carbon source. Samples for determination of cell concentration and for HPLC analysis were taken through an inserted, sterile needle and syringe.

Anaerobic Fermentations in a Fermenter

Some fermentations with industrial S. cerevisiae strains were conducted in an Infors Multifors fermenter (2×1.4l) with a working volume of 800 ml and equipped with temperature, pH, O2 and CO2 sensors. The fermenter was filled with 530 ml of concentrated fermentation medium (without carbon source and supplements) and then autoclaved. Prior to the start of the fermentation, 250 ml concentrated carbon source solution, 100 µl/l Antifoam 204 and the other supplements (vitamins, trace elements and antibiotics) were added to the concentrated medium. The fermenter was purged with nitrogen gas to initially create anaerobic conditions. A feed of nitrogen gas to the head space (0.4 l/min) was applied during the experiment to maintain anaerobic conditions. The gas outlet was cooled to condense and return vapor and then piped through a gas washing bottle. The culture was stirred with 300 rpm, temperature kept at 35° C. and pH kept at 5.0 by automated addition of 2M KOH or 2M $H_2PO_4$. The inoculum of cells (in 20 ml fermentation medium) was added when all set parameters were reached and constant. During the fermentations samples were taken for cell dry weight determination and HPLC analysis. Iris 5.2 Software (Infors) was used to operate the fermenter and monitor the experiment.

Determination of Cell Dry Mass

To determine cell dry mass 5-10 ml of a liquid culture were vacuum filtered through a pre-washed and dried (as described below) filter (nitrocellulose, pore size 0.45 µm) and subsequently washed twice with ddH2O. The filters were dried in a microwave oven at 120-150 W for 15 min and left to cool and dry further in a desiccator for another 15 min. The filters were weighted prior to filtering and after drying to measure the cell dry weight. The method described has been adapted from Ask et al. (Ask et al., 2013).

Evolutionary Engineering

The evolutionary engineering was done as an serial aerobic batch fermentation. Transformants were first inoculated in selective $SCE_2$ to obtain biomass and then grown in selective SC and SM medium with 20 g/l xylose to adapt the strain to xylose utilization. After these initial cultures the cells were switched to medium with 10 g/l xylose and increasing concentrations of glucose to apply an evolutionary pressure. When they were reaching late exponential to early stationary phase cells were harvested by centrifugation (2000×g, 2 min) and transferred to fresh medium to an $OD_{600}$ of 0.2. Glucose concentrations were increased every time an adaptation could be seen or growth was not negatively influenced by the current glucose concentration. To all media, liquid and solid, G418 was added to select for the AFY10 strain background. Liquid media additionally contained 0.5 g/l 2-deoxy-D-glucose (2-DOG) to suppress formation of suppressor mutants of the $hxk^0$ phenotype. $hxk^0$ strains, but not wild type strains, are resistant to 2-DOG (Subtil and Boles, 2012). Lack of glucose-consumption has been confirmed by streaking out culture samples on glucose-media-plates and also by HPLC analysis.

Metabolite Analysis by HPLC

For analysis of metabolites cell-free samples (5-10 min, 4° C., 16000×g) were mixed with ⅑ volumes of 50% (w/v) 5-sulfosalicylic acid and centrifuged (5-10 min, 4° C., 16000×g). The supernatant was analyzed in an UHPLC+ system by Thermo Scientific (Dionex UltiMate 3000) equipped with a HyperREZ XP Carbohydrate $H^+8$ µm column and a refractive index detector (Thermo Shodex RI-101). Separation was carried out at column temperature of 65° C. with 5 mM sulfuric acid as mobiles phase with a flow rate of 0.6 ml/min. Chromeleon 6.80 software was used to control the system and to analyze the data. Five standards (mixtures of D-glucose, D-xylose, xylitol, acetate, glycerol and ethanol with concentrations of 0.01-3% (w/v)) were analyzed for quantification of the different compounds.

Sugar Uptake Assays

Sugar uptake assays were done as described by Bisson et al. (Bisson and Fraenkel, 1983) with modifications according to Walsh et al. (Walsh et al., 1994).

Transformants of strain EBY.VW4000 were grown in selective YEPE to an OD of 1.1-1.6, harvested by centrifugation and washed twice in ice-cold uptake-buffer (RT, 3 min, 3000×g). Cells were kept on ice from here on. The cell pellet was resuspended in ice-cold uptake-buffer to a concentration of 60 $mg_{ww}$/ml and aliquoted to 110 µl. One cell suspension aliquot and one sugar solution were incubated in a water bath at 30° C. for 4-5 min. 100 µl of the cell suspension were pipetted to the sugar solution (50 µl), mixed briefly by pipetting and incubated for 5 (D-[U-$^{14}$C]-glucose) or 20 sec (D-[1-$^{14}$C]-xylose). The uptake reaction was stopped by transferring 100 µl of the mixture into 10 ml ice-cold quenching-buffer, which was immediately filtered through a Durapore membrane filter (0.22 µm pore size, Millipore). The filter was washed twice with 10 ml ice-cold quenching-buffer, transferred to a scintillation vial containing 4 ml scintillation cocktail (Rotiszint eco plus, Roth) and shaken thoroughly. Additionally to this filter sample ($cpm_{filter}$), 10 µl of each reaction were transferred directly to a scintillation vial with 4 ml scintillation cocktail for determination of the total counts in the reaction ($cpm_{total}$). To determine a value for sugar that is bound unspecifically to the cell surface or the filter (cpmblank) a few samples of 33,3 µl sugar solution and 66,6 µl cell suspension were mixed in 10 ml icecold quenching buffer and treated as described above. Radioactivity of all vials was analysed in an Wallac 1409 liquid scintillation counter.

Stocksolutions of 2M, 500 mM or 20 mM glucose or xylose (in $H_2O$) were used to prepare the sugar solutions for the assays (threefold of the desired concentration in the uptake reaction (S, substrate concentration), 50 µl aliquots). Uptake was measured at sugar concentrations 0.2, 1, 5, 25 and 100 mM for glucose and 1, 5, 25, 66, 100, 200 and 500 mM for xylose. Inhibition of xylose uptake by glucose was measured at 25, 66 and 100 mM xylose with additional 25 and 100 mM unlabelled glucose. Sugar solutions contained 0.135 to 0.608 µCi of D-[U-$^{14}$C]-glucose (290-300 mCi/mmol) or D-[1-$^{14}$C]-xylose (55 mCi/mmol) (American Radiolabeled Chemicals Inc., St. Louis, Mo., USA).

Data of the uptake assays were used for following calculations:

The amount of sugar ($A_{sugar}$ in nmol) taken up during the incubation time (t, in seconds) at a certain sugar concentration (S, in mM):

$$A_{sugar}=((cpm_{sample}-cpm_{blank})/(cpm_{total}\cdot 10))\cdot S\cdot 100 \text{ µl}$$

Transport velocity (in $nmol\cdot min^{-1}\cdot mg_{ww}^{-1}$) calculated per milligrams of cell (m, in $mg_{ww}$):

$$V=(A_{sugar}\cdot 60 \text{ s})/(t\cdot m)$$

Calculation of $K_m$ (Michaelis constant), $V_{max}$ (maximal initial uptake velocity) and $K_i$ (inhibitor constant for competitive inhibition) was done by nonlinear regression analysis and global curve fitting in Prism 5 (GraphPad Software, Inc.) with values of three independent measurements.

Bioinformatic Methods

DNA sequences were obtained from the *Saccharomyces* Genome Database (SGD, (Cherry et al., 2012)). Sequence alignments for transporter proteins were conducted using the PRALINE multiple alignment server ((Simossis and Heringa, 2005)) with standard settings plus PHOBIUS transmembrane structure prediction (KAil et al., 2004). Phylogenetic trees were calculated from PRALINE alignments with ClustalW2 phylogeny (Larkin et al., 2007) and visualized with Phylodendron software (http://iubio.bio.indiana.edu/soft/molbio/java/apps/trees/). Similarities and identities between protein sequences were calculated from PRALINE alignments using SIAS (http://imed.med.ucm.es/Tools/sias.html). Figures for sequence alignments were created with ALINE software (Bond and Schuttelkopf, 2009).

Example 1

N376Y

Mutants of GAL2 were created using error-prone PCR (epPCR) and then screened in AFY10X as described in Farwick et al. (2014). This method is faster than evolutionary engineering experiments and more often generates multiple mutations per ORF that might have a unique combined effect. On the downside, there might be more silent mutations among the increased number of mutations which might aggravate the identification of the relevant mutations in each clone. The GAL2 ORF was amplified in an epPCR with short amplification primers, applying various mutation rates, and the purified fragments then again amplified for recombinational cloning in a second PCR. Functional plasmids were in vivo assembled from PCR fragments and linearized p426H7 vector directly in the screening strain AFY10X. Transformants were plated out on selective $SCE_2$ plates and subsequently screened. Colonies were tested for improved growth on media with 1% xylose and increasing amounts of glucose (up to 5%) by replica-plating. Seven clones were selected and grown in $SCE_2$ ura⁻ leu⁻+G418+2-DOG and samples of these cultures streaked out on plates for comparison and to obtain single colonies. Five of these seven clones were confirmed to grow on xylose glucose media. The plasmids of two clones were successfully isolated as described (yeast DNA was digested with EcoRI) and sequenced. The sequencing revealed multiple amino acid mutations as can be seen in Table 1.

TABLE 1

Analysis of two clones of the epPCR-screening.

| clone | growth on medium (xylose + glucose) | mutations |
| --- | --- | --- |
| Gal2_ep3.1 | 1 + 5 | M107K V239L N376Y M435I L558S |
| Gal2_ep3.3 | 1 + 3 | T219S M255L R267C L299S N346I E528D |

Example 2

M435

2.1 Investigation of Gal2_ep3.1 Mutations

Based on the tests for functionality of Gal2_N376Y, it could be determined that it is not N376Y alone which is responsible for the properties of Gal2_N376Y. Therefore the further mutations of Gal2_ep3.1 should be investigated separately. N376Y is responsible for the reduced affinity for glucose and galactose. Thus the question is which amino acid is responsible for the improved uptake of xylose. For this reason the replacements M107K, V239L, M435I and L558S were made in the vector p426_Gal2_N376Y and then this vector was transformed into the screening strains EBY.VW4000 and AFY10 to test their properties with the aid of growth tests. It is expected that one or more amino acid exchanges determine the improved growth on xylose of Gal2_ep3.1. The position M435I is the only position to be examined, which is located in a transmembrane domain (TM10). The other positions are located in the loops or in the C-terminus. Apart from that the mutation N376Y can also be found in a transmembrane domain (TM8), whereas this mutation is located close to the sugar binding area. However M435I is located close to the upper membrane level.

2.2 Test for Functionality of the Ep3.1 Mutations

Figure 1:
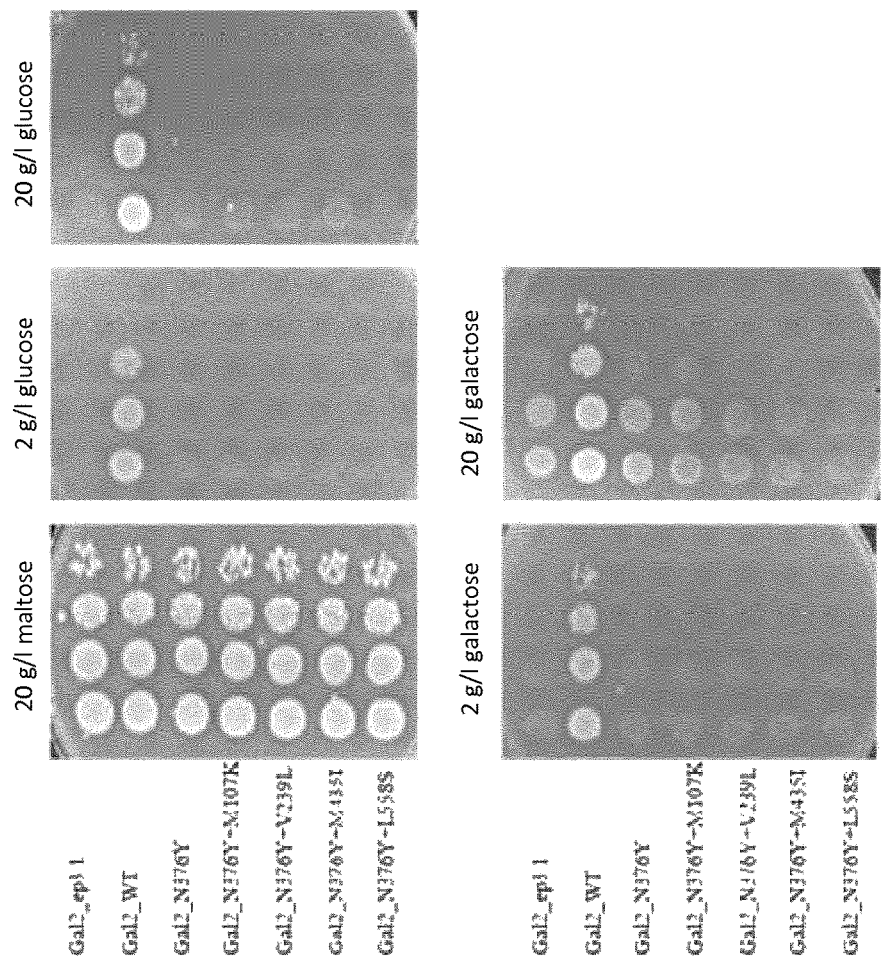
FIG. 1: Growth test of Gal2_ep3.1 mutants in comparison to N376Y in EBY.VW4000.

The screening strains EBY.VW4000 and AFY10 with the vectors which contained the respective mutated GAL2-sequence, were tested for their growth behavior. Therefore the constructs were tested in EBY.VW4000 on galactose, as well as glucose with different concentrations. None of the mutants showed significant growth. Because all of the constructs got the N376Y mutation, it was supposed that the effect to reduce the affinity for hexoses, was not affected by the additional mutations (FIG. 1).

The constructs were tested in AFY10 on xylose media, whereby a concentration of 0.2% was also chosen to test the transporters' xylose affinity. Furthermore the competitive inhibition by glucose was tested with media which contained xylose and glucose. It was observed that Gal2_N376Y+M435I showed similar growth like Gal2_ep3.1 on 2% xylose, as well as on 1% xylose with 4% glucose. Certainly Gal2_N376Y+M435I seems to have a higher xylose affinity, because it was observed a better growth on 0.2% xylose and 0.2% xylose with 2% glucose in comparison to Gal2_ep3.1.

Apart from that the wild type showed the best growth on low xylose concentrations without glucose. The mutants with the other ep3.1 mutations were not able to grow on xylose (FIG. 2).

2.3 Growth and Fermentation of Gal2 N376Y+M435I

To investigate the growth difference and the xylose consumption of the mutants in comparison to the wild type and the error prone mutant, an anaerobic growth test in liquid media was carried out. For this purpose AFY10 cells were co-transformed with the vector with the respective GAL2 sequence and YEp181_pHXT7-opt.XI_Clos and inoculated in SCE-ura-leu+G418 to have an $OD_{600}$ of 0.6 in 30 ml SC-ura-leu with 0.6% xylose or with 0.6% xylose with 2% glucose. The $OD_{600}$ was measured regularly during five days, the growth rate µ was determined and the metabolites of the samples were examined, whereby the samples were diluted 1:5 for this reason.

It was shown that the transformants with Gal2_N376Y+M435I with a growth rate of 0.014 $h^{-1}$ in 0.6% xylose resp. 0.015 $h^{-1}$ in 0.6% xylose with 2% glucose had the best growth in comparison to the wild type and the error prone mutant, that had only growth rates of 0.006 to 0.007 $h^{-1}$. The behavior of Gal2_N376Y+M435I in both of the used media was similar, which shows that there were no impairments by glucose. The transformant with Gal2_wt showed the biggest differences, because it could grow on media without glucose much better ($OD_{600}$ tend: 0,86 [Xyl] und 0,52 [Xyl+Glu]). This effect can be explained by the competitive inhibition of xylose uptake by glucose. Gal2_ep3.1 did not show significant differences regarding both media. Certainly the growth of this mutant is lower than the growth of the wild type in media with 0.6% xylose, but showed a better growth than the wild type with 2% glucose. Furthermore the growth of the transformants in general was low, because of the long generation time of AFY10, as well as xylose as the carbon source, which was very low concentrated and the required adaptation time to the new media.

Furthermore several metabolites were measured, especially the concentrations of xylose and glucose. The concentration of glucose in the media with 0.6% xylose and 2% glucose did not change as expected (data not shown), because AFY10 cannot metabolize glucose. The decrease of xylose concentration in the supernatant of the different strains correlates with the growth behavior. Therefore the highest consumption of xylose could be observed for Gal2_N376Y+M435I, because it showed the highest growth rate. The xylose concentration decreased during the fermentation to 0.35% resp. 0.37%. The transformants with Gal2_wt and Gal2_ep3.1 consumed less xylose, which was analogous to their growth behavior. Because of glucose inhibition, Gal2_wt in the media with 2% glucose consumed little xylose, whereas the xylose concentration decreased only to 0.53% (FIG. 3).

Example 3

M435/N376

3.1 Combination of M435I with Various Amino Acids at Position N376

In example 2 it is shown that the exchange of amino acid M435 to isoleucine could significantly improve growth of strains with the Gal2_N376Y mutation on glucose-xylose mixtures. To demonstrate whether M435 alone has an impact on sugar uptake, serial dilution drop tests were performed. It could be shown that on low xylose concentrations (2 g/L) growth of strains with a Gal2_N376F exchange was better than that of Gal2_N376Y+M435I. To find out the effect of M435I alone and in combination with N376F, corresponding mutants were constructed. To determine the kinetic properties of the various mutants, sugar uptake measurements with radioactively labelled xylose were performed.

3.2 Growth of Mutants with Gal2_M435I with Hexoses, Xylose and Sugar Mixtures

To see the effect of only the exchange of M435I on the uptake of glucose and galactose, the exchange was introduced into wild-type Gal2 and characterized by serial dilution drop tests with strain EBY.VW4000. As can be seen in FIG. 4, the M435I exchange had no effect on the uptake of galactose. Uptake of glucose is strongly reduced. As well with 2 g/l as also with 20 g/l glucose growth is much slower with the M435I mutation.

To test the effect of M435I on the uptake of xylose, Gal2_M435I together with construct YEp181_pHXT7-optXI_Clos was transformed into competent AFY10 cells and a drop test was performed. Due to the exchange of M435I also the uptake of xylose is reduced. No growth could be seen with 2 g/l xylose and only slow growth on 20 g/L xylose. No growth was visible on xylose-glucose mixtures (FIG. 5). These results demonstrate that M435I improves growth only in combination with other mutations, e.g. a mutation at position N376.

3.3 Growth of Mutants with Gal2_N376F+M435I with Xylose and Sugar Mixtures

To characterize the different constructs which all were verified by sequencing they were transformed together with vector YEp181_pHXT7-optXI_Clos into competent AFY10 cells and drop tests were performed.

Comparing growth of cells with N376Y+M435I with the other strains it becomes obvious that they grow faster on high concentrations of xylose (FIG. 6). As well with 20 g/l xylose as also with 10 g/l xylose plus 40 g/l glucose the N376Y+M435I strain shows the best growth. On low xylose concentrations cells containing the N376F+M435I combination grow the best. The additional mutation of M435I seems to improve N376F but only a little bit.

3.4 Kinetic Properties of N376/M435I Transporter Variants

Xylose uptake of Gal2_N376F, N376F+M435I, N376Y und N376Y+M435I was characterized with a sugar uptake assay. The relevant plasmids were transformed in strain EBY.VW4000. Cells were cultivated in SCM-ura until they reached the exponential growth phase ($OD_{600}$~0.6). Then cells were harvested, concentrated to the same $OD_{600}$ ($OD_{600}$ 35-40), separated into different aliquots and stored on ice.

Three uptake assays (in tripicates) were performed with different concentrations of radioactively labelled xylose. Data were collected and fittet with GraphPad Prism according to Michaelis Menten (FIGS. 7 and 8).

Mutation N376Y leads to a strong reduction in the uptake activity compared to the wild-type Gal2. However, N376Y+M435I shows a strongly improved xylose uptake rate, even significantly higher than the wild type.

Surprisingly and in contrast to the growth assays (FIG. 6), N376F+M435I seems to have a reduced uptake rate compared to the wild type and to N376F mutant alone.

From the fitted data the $K_m$-values and maximal uptake rates $V_{max}$ were determined (Table 2).

TABLE 2

From the uptake assays $K_m$ and $V_{max}$ were calculated for Gal2_variants N376F, N376Y, N376Y + M435I, N376F + M435I and Gal2 WT with standard deviations, according to Michaelis-Menten graph with GraphPad Prism.

|  | $V_{max}$ | Standard deviation | $K_m$ | Standard deviation |
|---|---|---|---|---|
| N376Y | 11.92 | 2.777 | 370.4 | 176.7 |
| N376Y + M435I | 99.61 | 28.76 | 711.4 | 314.1 |
| N376F | 25.86 | 2.458 | 108.9 | 35.73 |
| N376F + M435I | 13.81 | 2.280 | 110.8 | 48.94 |
| Gal2 WT | 63.43 | 11.58 | 617.4 | 176.2 |

It can be seen from Table 2 that $V_{max}$ of N376Y is strongly increased by the additional M435I mutation, even much higher than in the wild type. In the case of N376F $V_m$ is reduced by M345I. The $K_m$-values of N376F and N376F+M435I look very similar. Due to the high standard deviations it cannot be concluded that N376F+M435I has a higher affinity than N376F alone. The faster growth (FIG. 6) would indicate this. It seems that at least in vivo the additional M345I mutation improves growth of cells with the N376F at low xylose concentrations (2 g/l) (FIG. 6).

The features disclosed in the foregoing description, in the claims and/or in the accompanying drawings may, both separately and in any combination thereof, be material for realizing the invention in diverse forms thereof.

REFERENCES

Becker, J. and Boles, E. (2003) A modified *Saccharomyces cerevisiae* strain that consumes L-Arabinose and produces ethanol. *Appl Environ Microbiol* 69(7), 4144-50.

Brat D, Boles E, Wiedemann B (2009) Functional expression of a bacterial xylose isomerase in *Saccharomyces cerevisiae*. Appl Environ Microbiol. 75:2304-11.

Bruder S (2011) Analyse eines unbekannten Glukose Transporters in *Saccharomyces cerevisiae* und Entwicklung eines Xylose-Transporter Screening Systems. Diploma thesis (Goethe Universitat Frankfurt).

Demeke M M, Dietz H, Li Y, Foulquié-Moreno M R, Mutturi S, Deprez S, Den Abt T, Bonini B M, Liden G, Dumortier F, Verplaetse A, Boles E, Thevelein J M (2013) Development of a D-xylose fermenting and inhibitor tolerant industrial *Saccharomyces cerevisiae* strain with high performance in lignocellulose hydrolysates using metabolic and evolutionary engineering. Biotechnol Biofuels. 6:89.

Dien, B. S., Kurtzman, C. P., Saha, B. C. and Bothast, R. J. (1996) Screening for L-arabinose fermenting yeasts. *Appl Biochem Biotechnol* 57-58, 233-42.

Dietz H (2013) Konstruktion und Charakterisierung von pentosefermentierenden Industriehefestammen. PhD thesis. Goethe University Frankfurt, Germany Farwick A, Bruder S, Schadeweg V, Oreb M, Boles E. Engineering of yeast hexose transporters to transport D-xylose without inhibition by D-glucose. Proc Natl Acad Sci USA. 2014 Apr. 8; 111(14):5159-64.

Hahn-Hagerdal, B., Wahlbom, C. F., Gardonyi, M., van Zyl, W. H., Cordero Otero, R. R. and Jonsson, L. J. (2001) Metabolic engineering of *Saccharomyces cerevisiae* for xylose utilization. *Adv Biochem Eng Biotechnol* 73, 53-84.

Horak J and Wolf D H (1997) Catabolite inactivation of the galactose transporter in the yeast *Saccharomyces cerevisiae*: ubiquitination, endocytosis, and degradation in the vacuole. *J Bacteriol* 179(5):1541-1549.

Jeppson M, Bengtsson O, Franke K, Lee H, Hahn-Hagerdal B, Gorwa-Grauslund M F. (2006) The expression of a *Pichia stipitis* xylose reductase mutant with higher K(M) for NADPH increases ethanol production from xylose in recombinant *Saccharomyces cerevisiae*. Biotechnol Bioeng. 93(4):665-73.

Jin Y S, Jeffries T W. (2004) Stoichiometric network constraints on xylose metabolism by recombinant *Saccharomyces cerevisiae*. Metab Eng. 6(3):229-38.

Katahira S, Mizuike A, Fukuda H, Kondo A. (2006) Ethanol fermentation from lignocellulosic hydrolysate by a recombinant xylose- and cellooligosaccharide-assimiliating yeast strain. *Appl Microbiol Biotechnol*. 72(6):1136-43.

Kotter, P. and Ciriacy, M. (1993) Xylose fermentation by *Saccharomyces cerevisiae*. *Appl Microbiol Biotechnol* 38, 776-783.

Kou, S. C., Christensen, M. S. and Cirillo, V. P. (1970) Galactose transport in *Saccharomyces cerevisiae*. II. Characteristics of galactose uptake and exchange in galactokinaseless cells. *J Bacteriol* 103(3), 671-8.

Kuyper, M., Toirkens, M. J., Diderich, J. A., Winkler, A. A., van Dijken, J. P. and Pronk, J. T. (2005b) Evolutionary engineering of mixed-sugar utilization by a xylose-fermenting *Saccharomyces cerevisiae* strain. *FEMS Yeast Res* 5(10), 925-34.

Kuyper, M., Winkler, A. A., van Dijken, J. P. and Pronk, J. T. (2004) Minimal metabolic engineering of *Saccharomyces cerevisiae* for efficient anaerobic xylose fermentation: a proof of principle. *FEMS Yeast Res* 4(6), 655-64.

Lucas, C. and Uden, N. v. (1986) Transport of hemicellulose monomers in the xylose-fermenting yeast *Candida shehatae*. *Appl Microbiol Biotechnol* 23, 491-495.

Pitkanen J P, Rintala E, Aristidou A, Ruohonen L, Penttila M. (2005) Xylose chemostat isolates of *Saccharomyces cerevisiae* show altered metabolite and enzyme levels compared with xylose, glucose, and ethanol metabolism of the original strain. *Appl Microbiol Biotechnol*. 67(6): 827-37.

Reifenberger E, Boles E and Ciriacy M (1997) Kinetic characterization of individual hexose transporters of *Saccharomyces cerevisiae* and their relation to the triggering mechanisms of glucose repression. *Eur J Biochem* 245 (2):324-333.

Richard, P., Putkonen, M., Vaananen, R., Londesborough, J. and Penttila, M. (2002) The missing link in the fungal L-arabinose catabolic pathway, identification of the L-xylulose reductase gene. *Biochemistry* 41(20), 6432-7.

Sambrook J. and Russell D. W. (2001) *Molecular cloning. A laboratory manual*. New York: Cold Spring Harbor.

Subtil T and Boles E (2012) Competition between pentoses and glucose during uptake and catabolism in recombinant *Saccharomyces cerevisiae*. Biotechnol Biofuels 5(1):14.

Wieczorke, R., Krampe, S., Weierstall, T., Freidel, K., Hollenberg, C. P. and Boles, E. (1999) Concurrent knockout of at least 20 transporter genes is required to block uptake of hexoses in *Saccharomyces cerevisiae*. *FEBS Lett* 464(3), 123-8.

Wiedemann B., Boles E. (2008) Codon-optimized bacterial genes improve L-Arabinose fermentation in recombinant *Saccharomyces cerevisiae*. Appl Environ Microbiol. 74 (7):2043-50.

The invention claimed is:

1. A polypeptide, comprising at least one amino acid substitution at a position corresponding to M435 and at a position corresponding to N376 of the amino acid sequence of SEQ ID NO: 1, wherein the polypeptide has at least 80%, at least 90%, or at least 95% sequence identity with the amino acid sequence of SEQ ID NO: 1, and wherein the polypeptide has either or both of an in vitro and an in vivo pentose transport function.

2. The polypeptide of claim 1, wherein the polypeptide is Gal2 of *Saccharomyces cerevisiae*.

3. The polypeptide of claim 1, comprising the amino acid substitution M435I.

4. The polypeptide of claim 1, comprising an amino acid substitution that is selected from N376Y and N376F.

5. The polypeptide of claim 1, wherein the amino acid substitution at the position corresponding to M435 increases activity of either or both of the in vitro and the in vivo pentose transport function compared to said activity of the polypeptide without the amino acid substitution.

6. The polypeptide of claim 1, wherein the amino acid substitution at the position corresponding to M435 increases affinity of the polypeptide for a pentose compared to said affinity of the polypeptide without the amino acid substitution.

7. The polypeptide of claim 1, wherein the pentose for which the polypeptide has pentose transport function is either one or both of D-xylose and L-arabinose.

8. A nucleic acid molecule, comprising a nucleic acid sequence encoding the polypeptide of claim 1.

9. The nucleic acid molecule of claim 8, further comprising one or more of:
(i) a vector nucleic acid sequence,
(ii) an expression vector sequence,
(iii) a promoter nucleic acid sequence,
(iv) a terminator nucleic acid sequence,
(v) a regulatory nucleic acid sequence,
wherein the nucleic acid molecule comprises dsDNA, ssDNA, PNA, CNA, RNA, or mRNA, or combinations thereof.

10. A host cell containing the nucleic acid molecule of claim 8, wherein one or more of:
(a) the host cell expresses said nucleic acid molecule,
(b) the host cell is a fungus cell,
(c) the host cell is a yeast cell, or
(d) the host cell is selected from the group consisting of a *Saccharomyces* species, a *Kluyveromyces* sp., a *Hansenula* sp., a *Pichia* sp., and a *Yarrowia* sp.

11. The host cell of claim 10, which belongs to the species *Saccharomyces cerevisiae*.

12. The host cell of claim 10, which has an increased uptake rate for either or both of D-xylose and L-arabinose, compared to a cell that does not contain the nucleic acid molecule encoding the polypeptide having either or both of in vitro and in vivo pentose transport function.

13. The host cell of claim 10 which further comprises either or both of:
(a) nucleic acid molecules which code for proteins of a xylose metabolic pathway, and
(b) nucleic acid molecules which code for proteins of an arabinose metabolic pathway.

14. The host cell of claim 13, which has at least one of:
(a) an increased rate of consumption of either or both of D-xylose and L-arabinose, or
(b) a faster growth rate with either or both of D-xylose and L-arabinose present,
compared to a cell that does not contain the nucleic acid molecule encoding the polypeptide having either or both of in vitro and in vivo pentose transport function.

15. The host cell of claim 13 wherein:
(i) the proteins of the xylose metabolic pathway comprise at least xylose isomerase and xylulokinase, and
(ii) the proteins of the arabinose metabolic pathway comprise at least rabinose isomerase, ribulokinase, and ribulose-5-P 4-epimerase.

16. A method for producing ethanol and/or other fermentation products, comprising expressing, in the host cell of claim 10, the nucleic acid molecule encoding the polypeptide having either or both of in vitro and in vivo pentose transport function.

17. The method of claim 16 which comprises recombinant fermentation by the host cell of biomaterial containing pentoses, wherein the pentoses comprise either or both of D-xylose and L-arabinose.

18. The method of claim 16 wherein the other fermentation products are selected from:
1-butanol, isobutanol, 2-butanol, other alcohols,
lactic acid, acetic acid, succinic acid, malic acid, other organic acids,
amino acids, alkanes, terpenes, isoprenoids, solvents, pharmaceutical compounds, and vitamins.

\* \* \* \* \*